(12) United States Patent
Hoffman et al.

(10) Patent No.: US 7,364,702 B2
(45) Date of Patent: Apr. 29, 2008

(54) LIQUID DISPENSING DEVICE

(76) Inventors: John Hoffman, 13823 Terrilee Dr., Poway, CA (US) 92064; John A. Adams, 9785 Running Creek La., Escondido, CA (US) 92026; Brian L. Ganz, 7057 Leeward St., Carlsbad, CA (US) 92009; David W. Jewell, 4019 Carmel View Rd., #156, San Diego, CA (US) 92130; John Andrew Moulds, 423 Jolina Way, Encinitas, CA (US) 92024; Janet M. Newman, 736 Arden Dr., Encinitas, CA (US) 92024

( * ) Notice: Subject to any disclaimer, the term of this patent is extended or adjusted under 35 U.S.C. 154(b) by 882 days.

(21) Appl. No.: 10/764,710

(22) Filed: Jan. 24, 2004

(65) Prior Publication Data
US 2005/0164403 A1      Jul. 28, 2005

(51) Int. Cl.
*B01L 3/02* (2006.01)

(52) U.S. Cl. .................. 422/100; 422/99; 422/101; 422/102; 222/181.1; 222/548; 436/180

(58) Field of Classification Search .......... 422/99–102; 222/181.1, 548; 436/180
See application file for complete search history.

*Primary Examiner*—Jill Warden
*Assistant Examiner*—Jyoti Nagpaul
(74) *Attorney, Agent, or Firm*—John R. Ross; John R. Ross, III

(57) ABSTRACT

A liquid dispensing device. The liquid dispensing device has a tray for holding a liquid at a relatively constant level. A syringe is used for drawing fluid from the tray. A liquid container containing a liquid is positioned upside-down in the tray such that the opening of the liquid container defines a vertical position that is slightly below the liquid level in the tray. Atmospheric pressure on the liquid in the tray and a vacuum inside the liquid container prevents liquid from draining from the container until the fluid level in the tray drops to a level approximately equal to the vertical position of the opening. The positioning of the syringe for drawing fluid is simplified by reason of the fact that the level of fluid in the tray is maintained at an approximately constant level despite withdrawal of quantities of fluid from the tray.

48 Claims, 21 Drawing Sheets

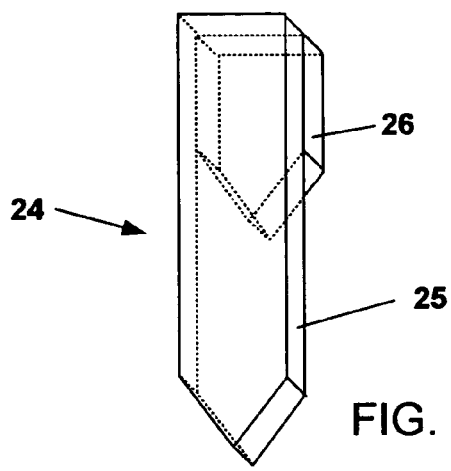
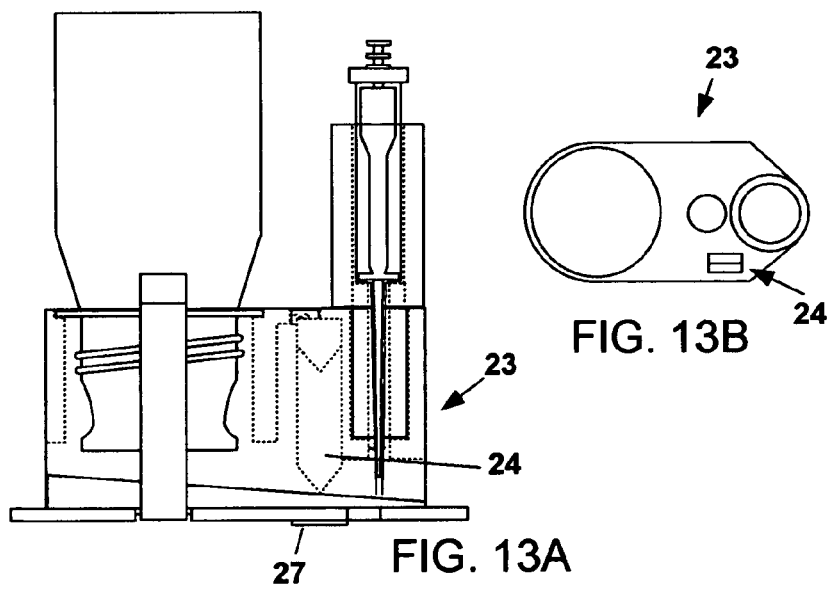
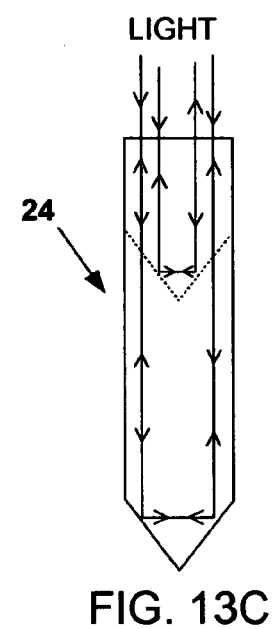
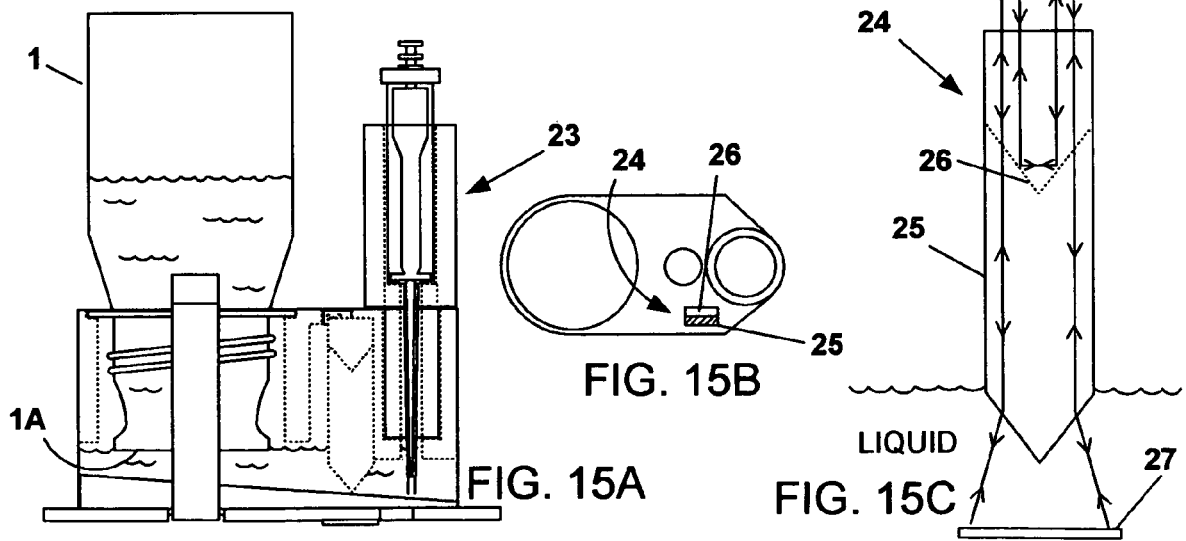
FIG. 14
FIG. 13B
FIG. 13C
FIG. 13A
FIG. 15A
FIG. 15B
FIG. 15C

LIQUID DISPENSING DEVICE

The present invention relates to liquid handling devices, and in particular, to liquid dispensing devices.

BACKGROUND OF THE INVENTION

Chemical solutions may be mixed either manually by a chemist or laboratory technician or they may be mixed automatically by an automated liquid mixing device. A syringe (also known as a pipette, pipettor or a micropipettor) may be used to transfer liquid from a bottle to a location where liquids are mixed, such as a micro-well plate.

For example, FIG. 1A shows prior art syringe 5 positioned over bottle 1B containing a liquid. In FIG. 1B, a technician has immersed the tip of syringe 5 into the liquid in bottle 1B. In FIG. 1C, the technician has pulled upward on plunger 6 with one hand while holding the bottom part of syringe 5 down with the other hand. Pulling upward on plunger 6 draws liquid into syringe 5. Syringe 5 can now be used for liquid dispensing.

There are problems with the prior art method of liquid dispensing illustrated in FIGS. 1A-1C. To draw liquid into the syringe it is only necessary to slightly immerse the tip of the syringe below the level of the liquid surface, as shown in FIG. 1D. However, a technician will typically over-immerse the syringe into the liquid. For example, as shown in FIG. 1C, the end of syringe 5 has been immersed far below the surface of the liquid in bottle 1B. As a result, after syringe 5 is removed from the liquid in bottle 1B, there will be an unnecessarily large amount of liquid adhered to the outside surface of syringe 5. This liquid can drip off, causing a mess and possibly causing contamination in the laboratory.

There are also similar problems with prior art automated liquid mixing devices. As with the manual method, prior art automated pipettors are ineffective at placing the syringe at the optimum level inside bottle 1B to prevent unnecessary liquid adhesion to the outside surface of syringe 5. The challenge for the prior art automated systems has been that as liquid is gradually removed from its bottle, the surface level of the liquid inside the bottle gradually decreases. Prior art systems have been unsuccessful in adjusting the degree to which the syringe is inserted into the bottle to appropriately account for the varying amount of liquid inside the bottle.

What is needed is a better liquid dispensing device.

SUMMARY OF THE INVENTION

The present invention provides a liquid dispensing device. The liquid dispensing device has a tray for holding a liquid at a relatively constant level. A syringe is used for drawing fluid from the tray. A liquid container containing a liquid is positioned upside-down in the tray such that the opening of the liquid container defines a vertical position that is equal to or just slightly below the liquid level in the tray. Atmospheric pressure on the liquid in the tray and a vacuum inside the liquid container prevents liquid from draining from the container until the fluid level in the tray drops to a level just below the vertical position of the opening. The positioning of the syringe for drawing fluid is simplified in that the level of fluid in the tray is maintained at an approximately constant level despite withdrawal of quantities of fluid from the tray.

BRIEF DESCRIPTION OF THE DRAWINGS

FIGS. 13A-16C show a second preferred embodiment of the present invention.

DETAILED DESCRIPTION OF THE PREFERRED EMBODIMENTS

Figure 8:
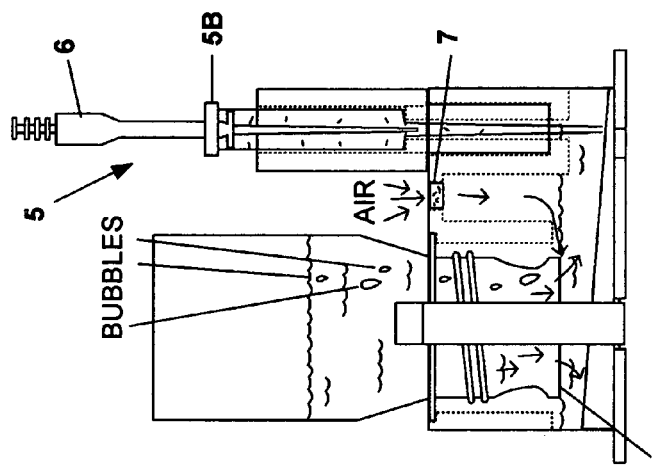
Figure 9:
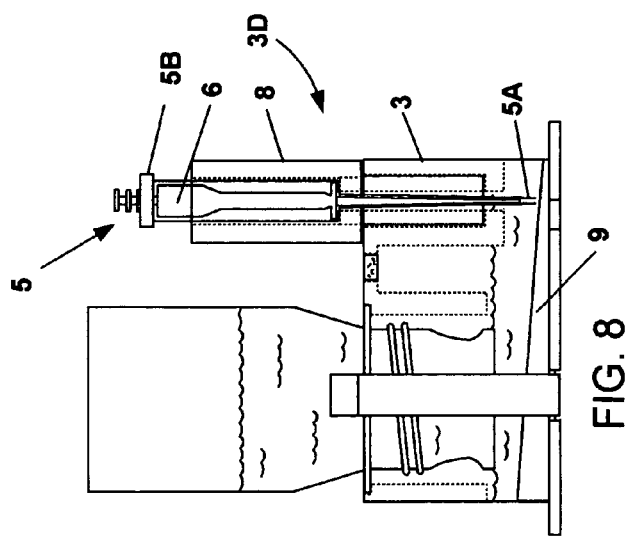
Figure 10:
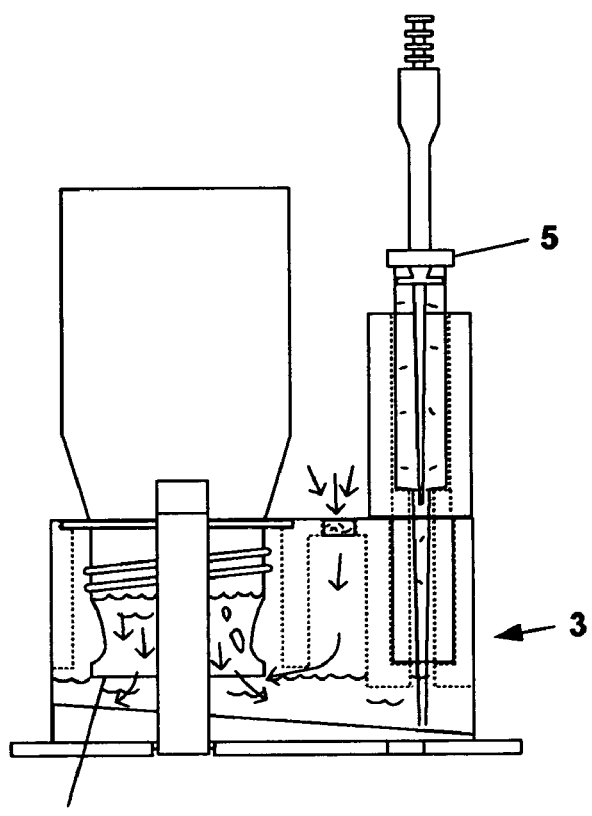
Figure 11:
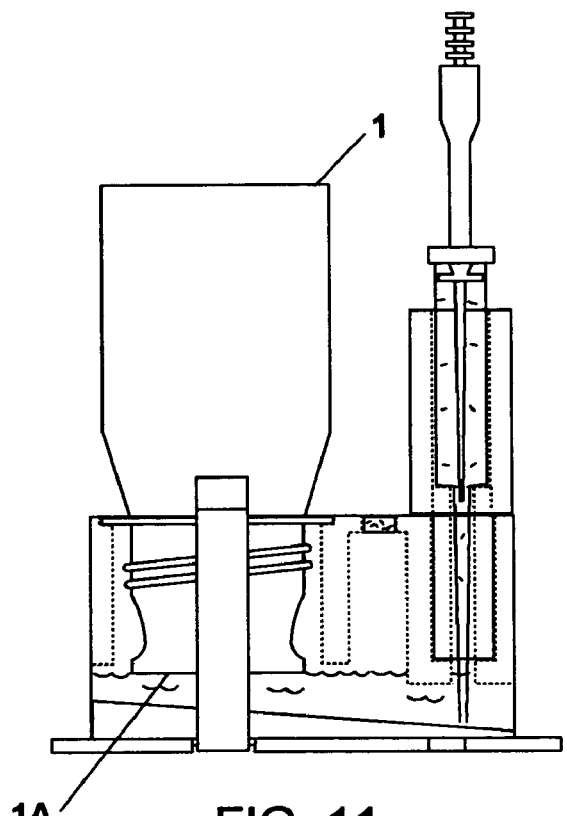

In a preferred embodiment of the present invention, tray 3 (FIG. 8) maintains an approximately constant dispensing level equal to or slightly above opening 1A of bottle 1 for syringe 5 as liquid is dispensed out of tray 3 (see FIGS. 9-11). By maintaining an approximately constant dispensing level, a laboratory technician or an automated dispensing device can more effectively and with less mess and error remove liquid from tray 3.

Manual Dispensing

First Preferred Embodiment

Liquid Dispenser

Figure 1A:
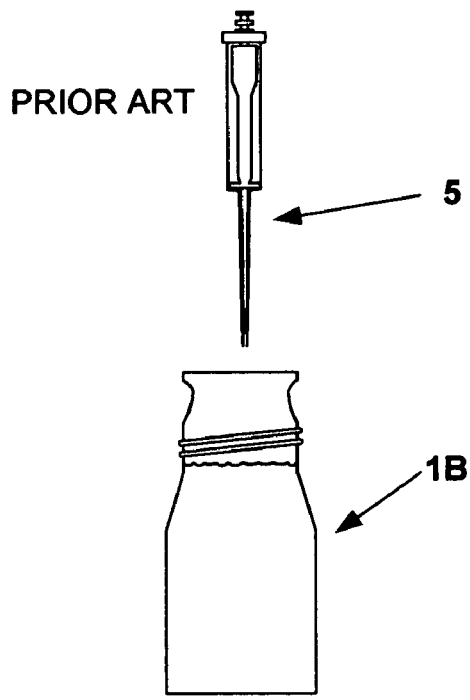
FIGS. 1A-1D show prior art methods for dispensing liquid from a bottle.
Figure 1B:
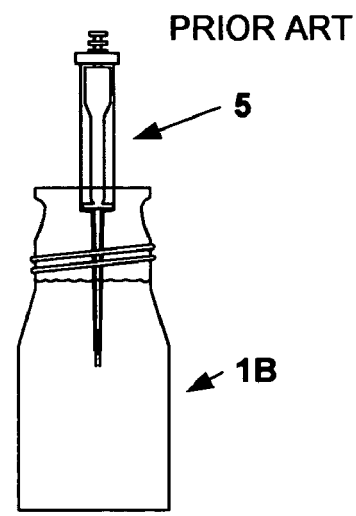
Figure 1C:
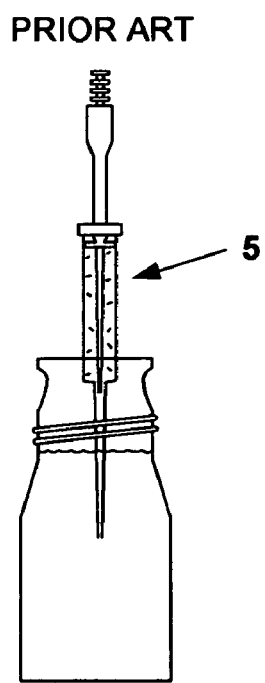
Figure 1D:
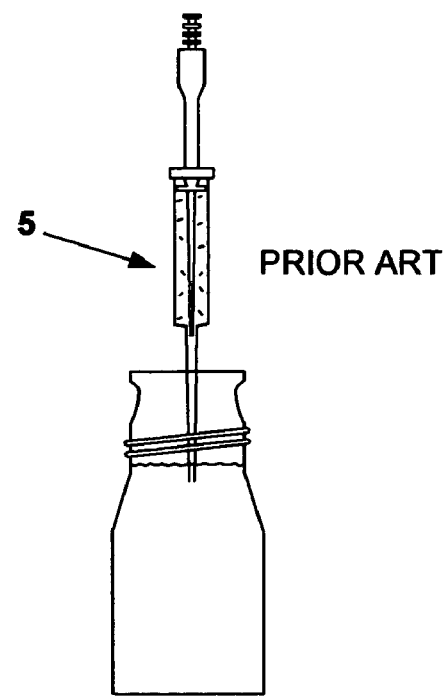
Figure 2A:
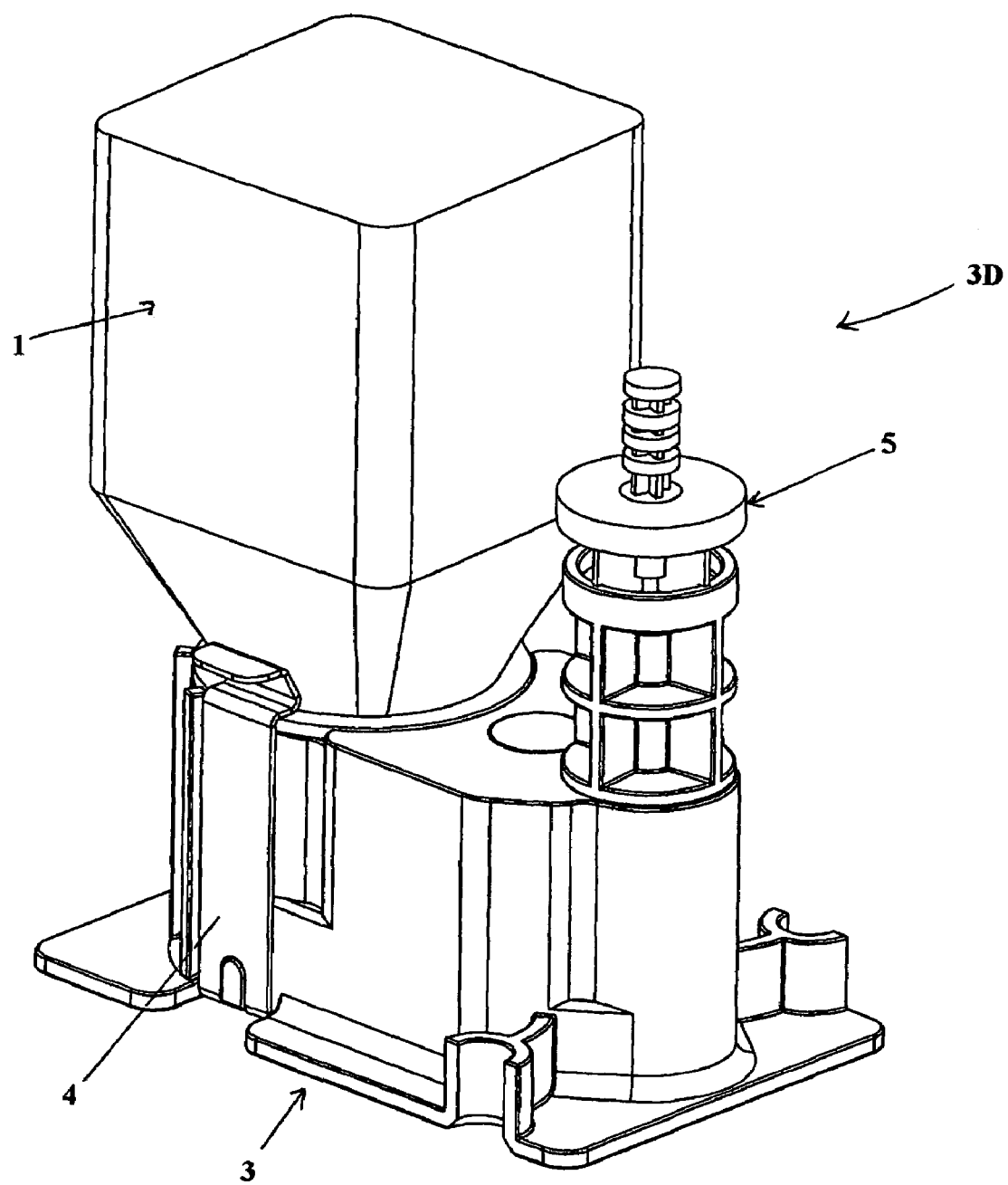
FIG. 2A shows a detailed perspective view of a first preferred embodiment of the present invention.
Figure 2B:
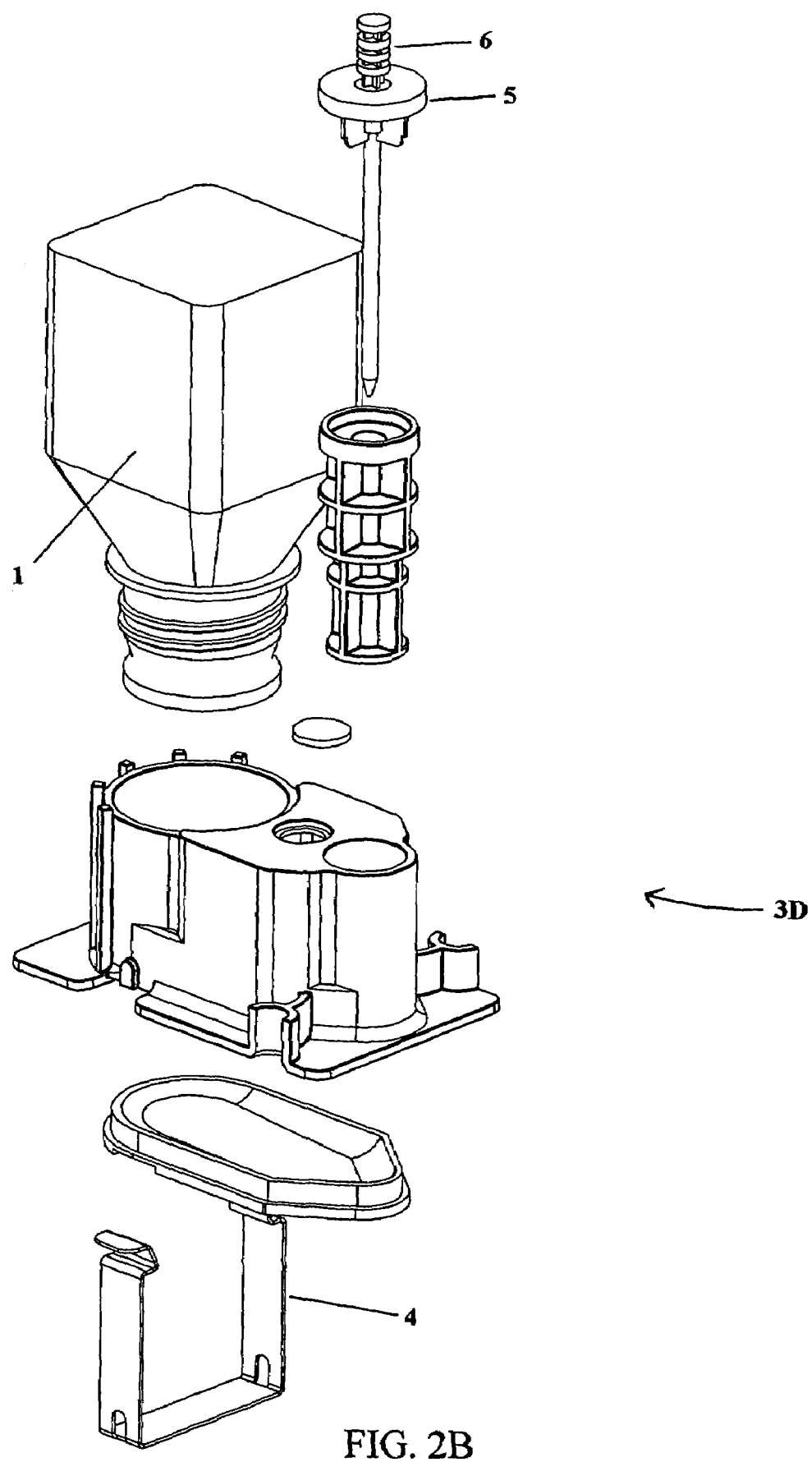
FIG. 2B shows a detailed exploded perspective view of a first preferred embodiment of the present invention.
Figure 3:
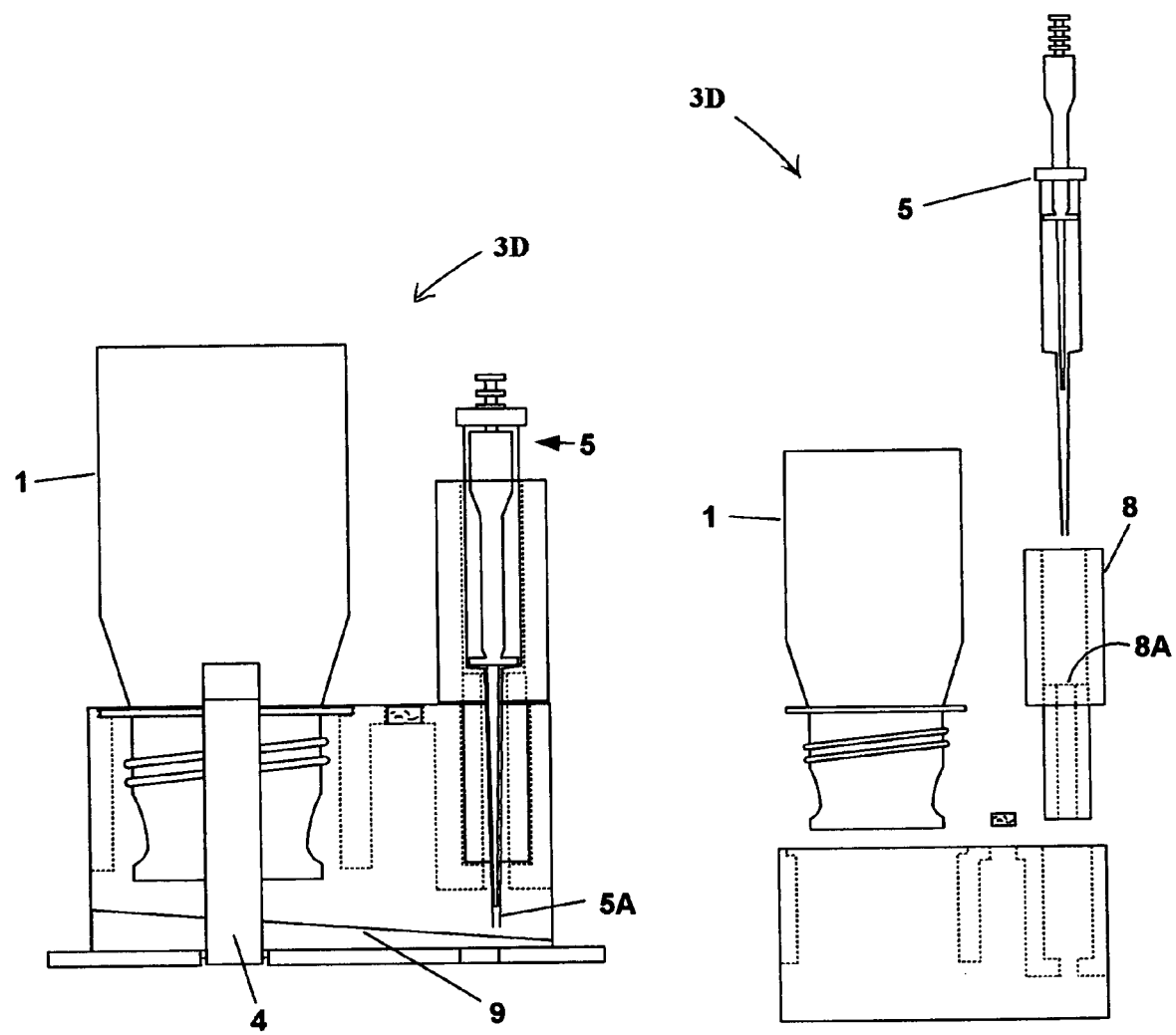
FIGS. 3 and 4 show a simplified front view and exploded view, respectively, of the first preferred embodiment.
Figure 4:
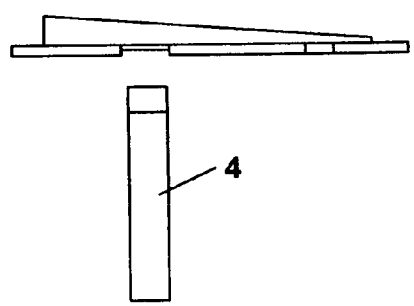

FIG. 2A shows a detailed perspective view and FIG. 2B shows a detailed exploded perspective view of liquid dispenser 3D. Likewise, FIGS. 3 and 4 show a simplified front view and exploded view, respectively, of liquid dispenser 3D.

In the first preferred embodiment, liquid to be dispensed is contained in upside-down bottle 1. As shown in FIG. 8, upside-down bottle 1 is held in place on top of tray 3 via metal bottle retaining clip 4. Preferably, tray 3 is fabricated from clear plastic. In the first preferred embodiment, a controlled amount of liquid flows out of bottle 1 and enters tray 3 where it is maintained inside tray 3 at an approximately constant level equal to or just slightly above the level of the level of the opening of bottle 1 as shown at 1A in FIG. 9. The liquid can then be easily removed by syringe 5 for further dispensing.

Operation of the First Preferred Embodiment

Figure 5:
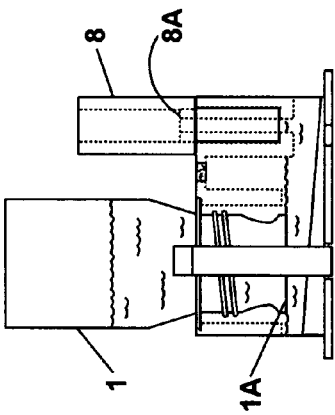
FIGS. 5-12 show the operation of the first preferred embodiment of the present invention.

Prior to attaching bottle 1 to tray 3, bottle 1 is filled with liquid to be dispensed. FIG. 5 shows a side view of bottle 1 containing liquid.

Figure 6:
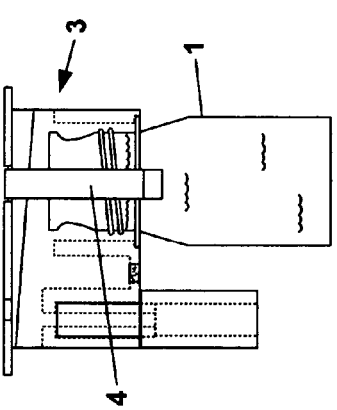

In FIG. 6, tray 3 has been snap-fitted on top of bottle 1. Bottle 1 is preferably held in place via metal retaining clip 4 (also shown in more detail in FIG. 2A).

Figure 7:
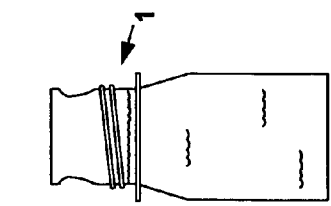

In FIG. 7, tray 3 and bottle 1 have been flipped over so bottle 1 is upside-down. A portion of the liquid that was in bottle 1 has flowed out of bottle 1 and into tray 3. The liquid will continue to flow out of bottle 1 until the level of liquid inside tray 3 is equal to or just slightly above the level of opening 1A of bottle 1. The combined effects of 1) atmospheric pressure exerting its force onto the surface of the liquid inside tray 3 and 2) the vacuum formed inside bottle 1 counter the effects of gravity and function to prevent the remainder of the liquid inside bottle 1 from emptying.

In FIG. 8, syringe 5 has been inserted into syringe holder 8 of tray 3. Syringe holder 8 includes abutment 8A (as shown in FIG. 4 and FIG. 7). Abutment 8A prevents further downward movement of syringe 5 and controls the location of tip 5A of syringe 5 so that tip 5A extends below the surface of the liquid inside tray 3 to a position just above the level of tilted bottom component 9 as shown in FIG. 8 (see also FIG. 3).

In FIG. 9, a user has grabbed syringe plunger 6 with one hand and has pulled it upward while holding syringe body 5B down with the other hand. The upward movement of syringe plunger 6 has caused liquid from tray 3 to be drawn up inside syringe 5. As liquid is drawn up inside syringe body 5B, the surface level of the liquid inside tray 3 decreases until eventually the level is below the level of opening 1A. Air is able to enter tray 3 via air filter 7. As the surface level decreases below the level of opening 1A, the vacuum inside bottle 1 will be momentarily broken as air is able to enter bottle 1 and flow upward as air bubbles through the liquid in bottle 1. As the air bubbles are flowing upward, liquid inside bottle 1 is filling tray 3. Liquid will continue to flow out of bottle 1 until once again the level of liquid inside tray 3 is equal to or slightly above the level of opening 1A of bottle 1, sealing off opening 1A and allowing the vacuum inside bottle 1 to reestablish.

In this fashion, liquid can be removed from tray 3 by syringe 5. After liquid has been removed from tray 3 via syringe 5, the user utilizes syringe 5 to deposit the removed liquid into a liquid receptacle device. For example in the first preferred embodiment, utilizing syringe 5, the user transfers liquid from tray 3 to a well in a micro-well plate.

While liquid is being removed, tray 3 maintains the level of the liquid inside tray 3 at a level equal to or just slightly above the level of opening 1A of bottle 1. For example, in FIG. 10 a user utilizing syringe 5 has removed a significant amount of liquid from tray 3 so that the level of liquid inside bottle 1 has decreased to level much lower than that shown in FIG. 9. However, the level inside tray 3 will rise until it is equal to or just slightly above the level of opening 1A. In FIG. 11, the user has removed even more of the liquid from tray 3 so that bottle 1 is approximately empty. The level of the liquid inside tray 3 is approximately equal to the level of opening 1A.

Figure 12:
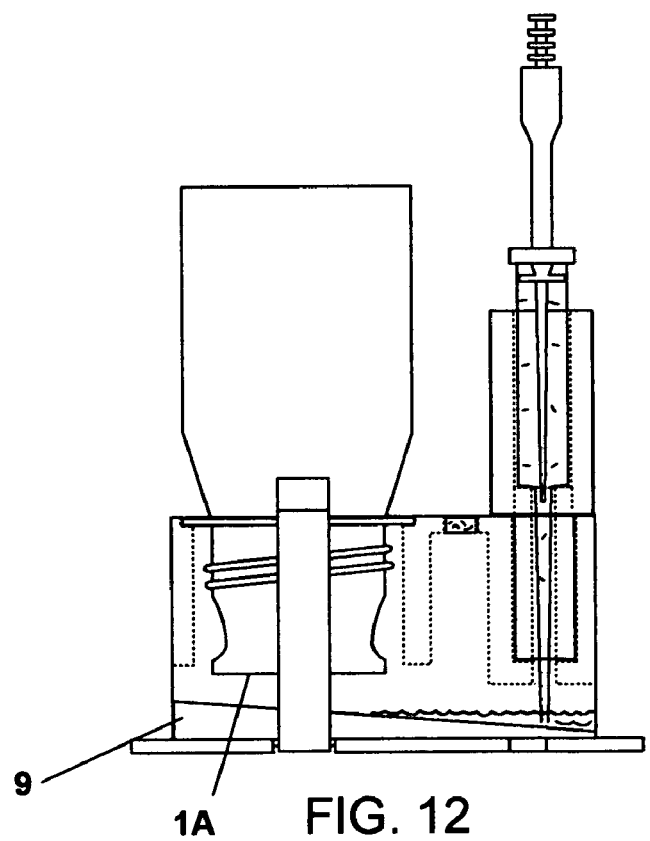

In FIG. 12, even more liquid has been removed from tray 3. After all the liquid has been removed from bottle 1, the user continues to remove liquid from tray 3, causing the level of the liquid to go below that of opening 1A. Tilted bottom component 9 has caused the remaining liquid inside tray 3 to puddle below the area of syringe 5 so that liquid can still be easily removed.

Second Preferred Embodiment

A second preferred embodiment is shown in FIGS. 13A and 13B. In the second preferred embodiment, tray 23 includes liquid level indicator 24. Below liquid level indicator is black tape strip 27. A detailed perspective view of liquid level indicator 24 is shown in FIG. 14. In the second preferred embodiment, liquid level indicator 24 is fabricated from clear plastic. Preferably, liquid level indicator 24 includes both low level indicator 25 and high level indicator 26.

Operation of the Second Preferred Embodiment

In FIG. 13A, liquid tray 23 is empty. This will cause light rays entering liquid level indicator 24 to be totally internally reflected as shown in FIG. 13C. Therefore, a user looking down onto the top of tray 23 will see that both low level indicator 25 and high level indicator 26 of liquid indicator 24 appear to be whitish, as shown in FIG. 13B.

In FIG. 15A, liquid tray 23 is filled so that the level of the liquid in tray 23 is slightly above the level of opening 1A. As explained above in reference to the first preferred embodiment, the preferred level of the liquid in tray 23 is equal to or just slightly above the level of opening 1A. In FIG. 15A, the pointed tip of low level indicator 25 is submerged in the liquid in tray 23 and the pointed tip of high level indicator 26 is above the liquid in tray 23. Because the pointed tip of low level indicator is submerged, light rays entering low level indicator 25 will be refracted as shown in FIG. 15C so that they will be partially absorbed and partially reflected by black tape strip 27. Conversely, because the pointed tip of high level indicator 26 is above the liquid in tray 3, light rays entering high level indicator 26 will be totally internally reflected. Therefore, a user looking down onto the top of tray 23 will see that low level indicator 25 appears to be black and that high level indicator 26 appears to be whitish, as shown in FIG. 15B.

Figure 16C:
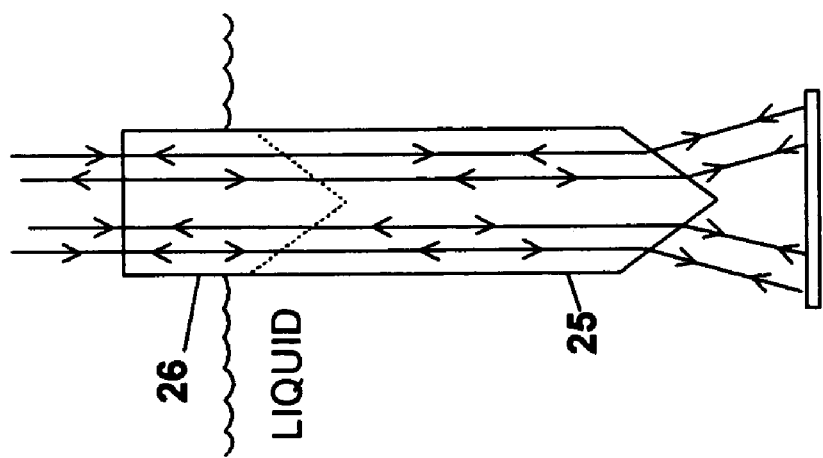
Figure 16B:
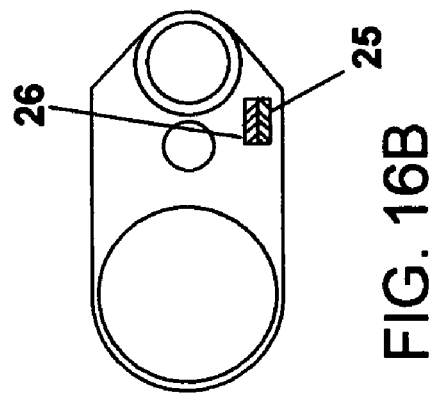
Figure 16A:
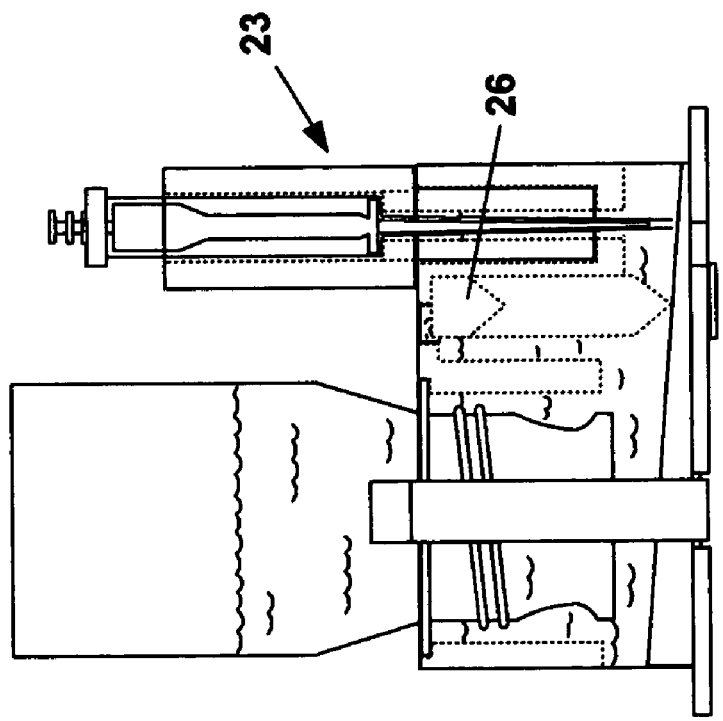

Although liquid tray 23 functions to keep the level of liquid inside tray 23 at a level equal to or just slightly above opening 1A as shown in FIG. 15A, the level inside tray 23 can rise to a higher level if, for example, tray 23 is inadvertently bumped or tilted breaking the vacuum inside bottle 1 and allowing air to enter bottle 1. In FIG. 16A, liquid tray 23 is filled so that the level of the liquid in tray 23 is above the level of high level indicator 26. The pointed tips of both low level indicator 25 and high level indicator 26 are submerged in the liquid in tray 23. Because the pointed tips of both level indicators are submerged, light rays entering level indicators 25 and 26 will be refracted as shown in FIG. 16C so that they will be partially absorbed and partially reflected by black tape strip 27. Therefore, a user looking down onto the top of tray 23 will see that low level indicator 25 and high level indicator 26 appear to be black, as shown in FIG. 16B.

Automated Liquid Handling Device

Third Preferred Embodiment

A third preferred embodiment is shown in FIGS. 17 to 42. In the third preferred embodiment an array of liquid dispensers similar to the dispensers described above are situated on platform 30 (FIG. 17). Computer 32 is programmed to automatically position robotic syringe grabber 31 over a selected liquid dispenser. Robotic syringe grabber 31 then automatically grabs syringe 5 from the selected liquid dispenser and draws liquid into the syringe in a fashion similar to that described above in reference to earlier preferred embodiments. Because the liquid dispensers situated on platform 30 maintain the level of the liquid to be dispensed at an approximately constant level. Syringe 5 is positioned so that its tip is submerged an optimum distance into the liquid to be dispensed. Therefore, robotic syringe grabber 31 does not have to be programmed to account for varying liquid levels. Robotic syringe grabber 31 then transfers the liquid to a liquid receiving device (such as micro-well plate 33A) where the liquid is dispensed.

Example of Operation of Third Preferred Embodiment

Figure 17:
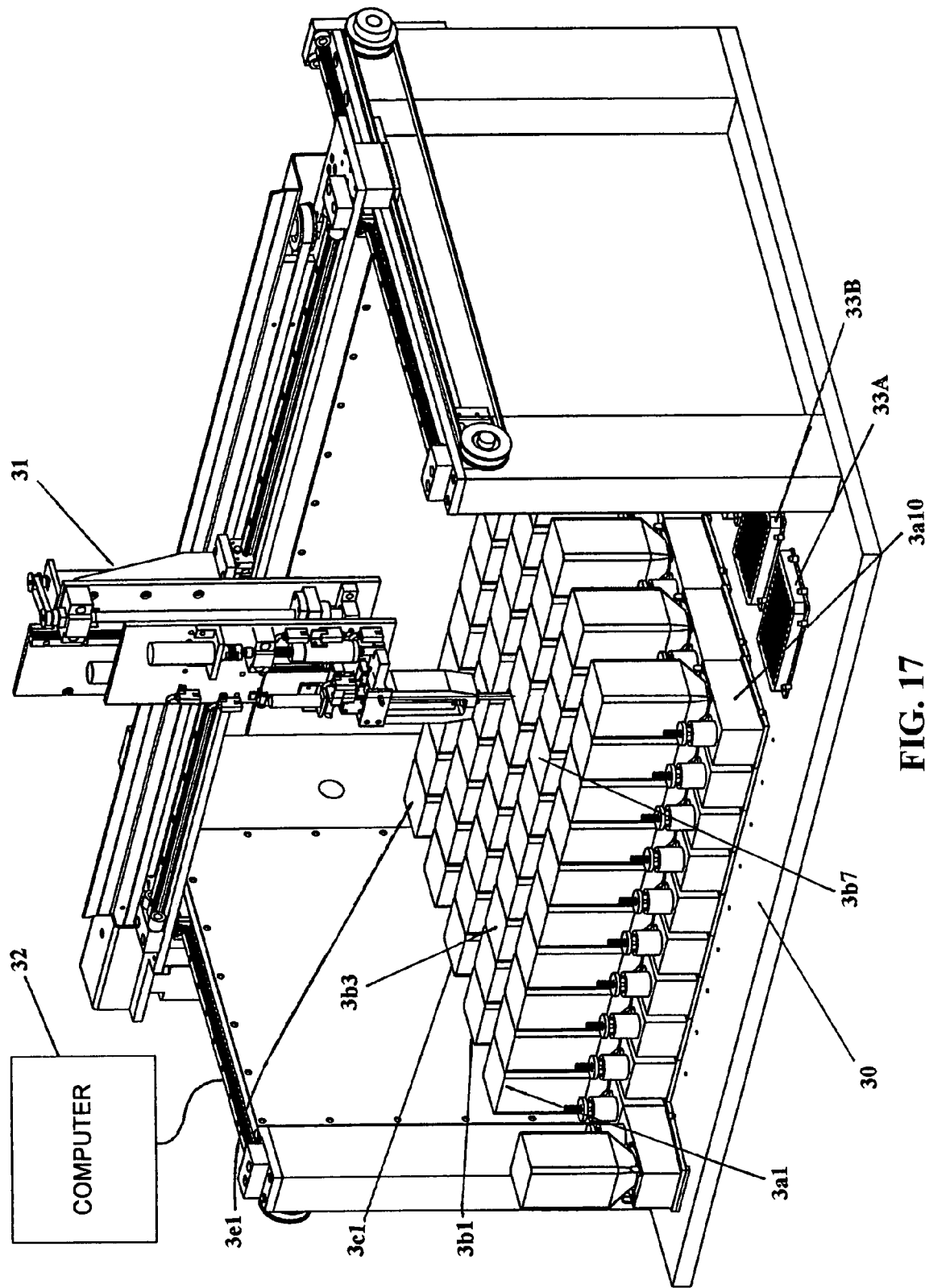
FIG. 17 shows a perspective view of a third preferred embodiment of the present invention.
Figure 18:
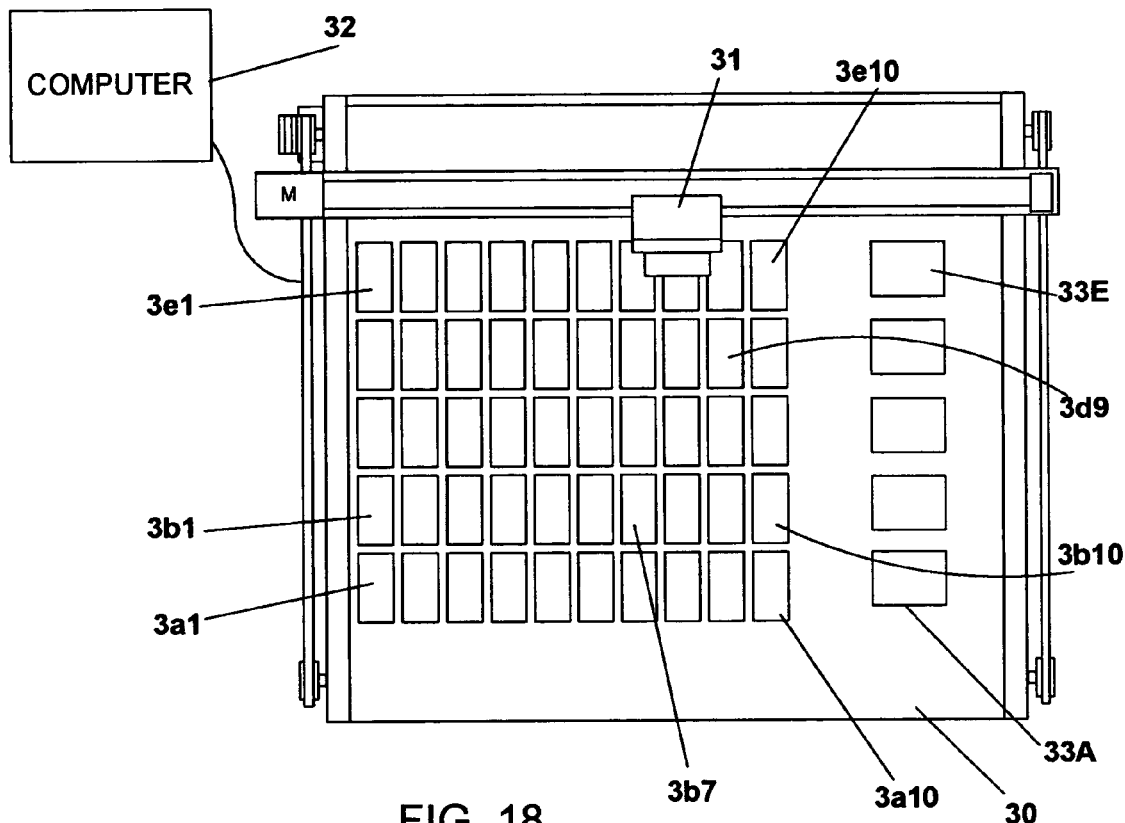
FIGS. 18-42 show the operation of the third preferred embodiment of the present invention.
Figure 19:
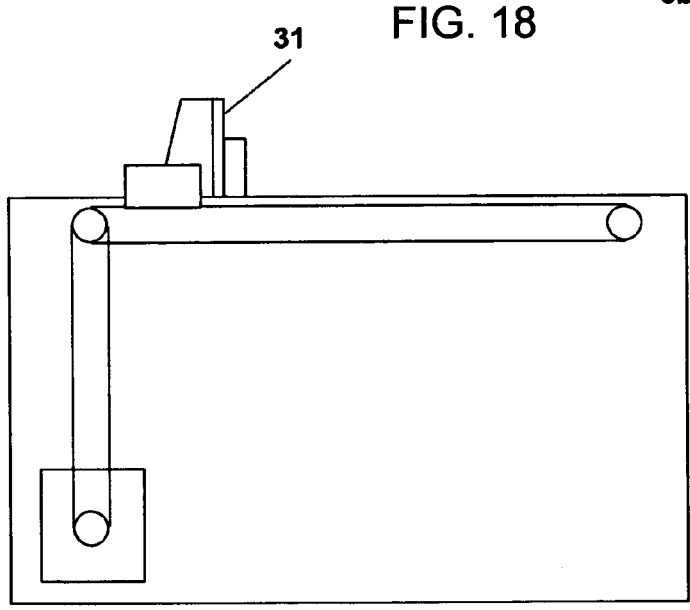

A detailed perspective view of the third preferred embodiment is shown in FIG. 17. A top view and left side view is shown in FIGS. 18 and 19, respectively. Dispensers 3a1-3e10 and micro-well plates 33a-33e are arranged on platform 30. Dispensers 3a1-3e10 are each similar to liquid dispenser 3D described above. Robotic syringe grabber 31 is controlled by computer 32. In the third preferred embodiment, computer 32 is programmed to control robotic syringe grabber 31 to draw liquid into syringes 5 of the selected dispensers. Robotic syringe grabber 31 is then controlled by computer 32 to remove syringes 5 from the selected dispensers and transfer the liquid in the syringe to pre-selected micro-well plates.

In the following example, computer 32 is programmed to control robotic syringe grabber 31 to remove syringe 5 located in dispenser 3b7 and transfer the liquid to micro-well plate 33a.

Figure 20:
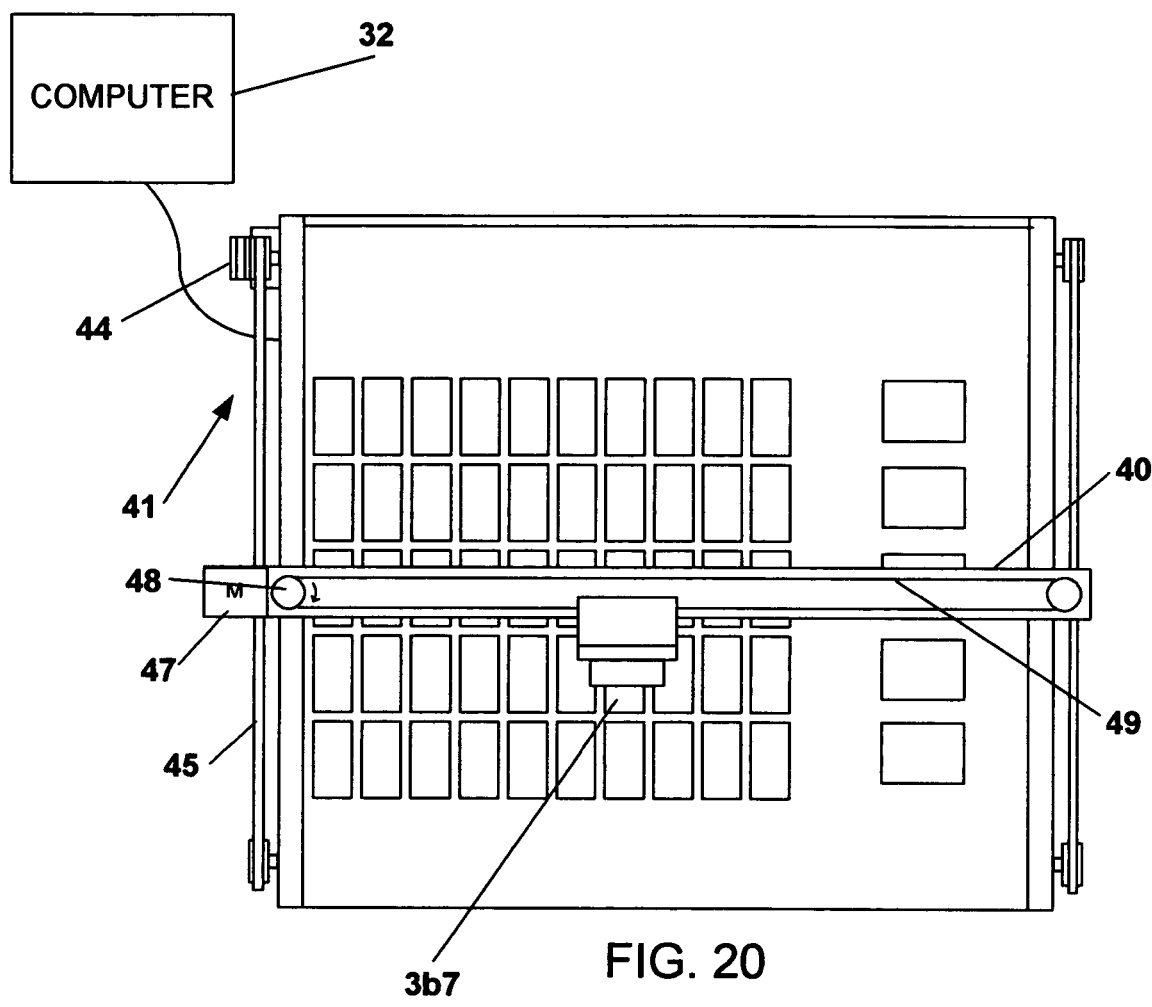
Figure 21:
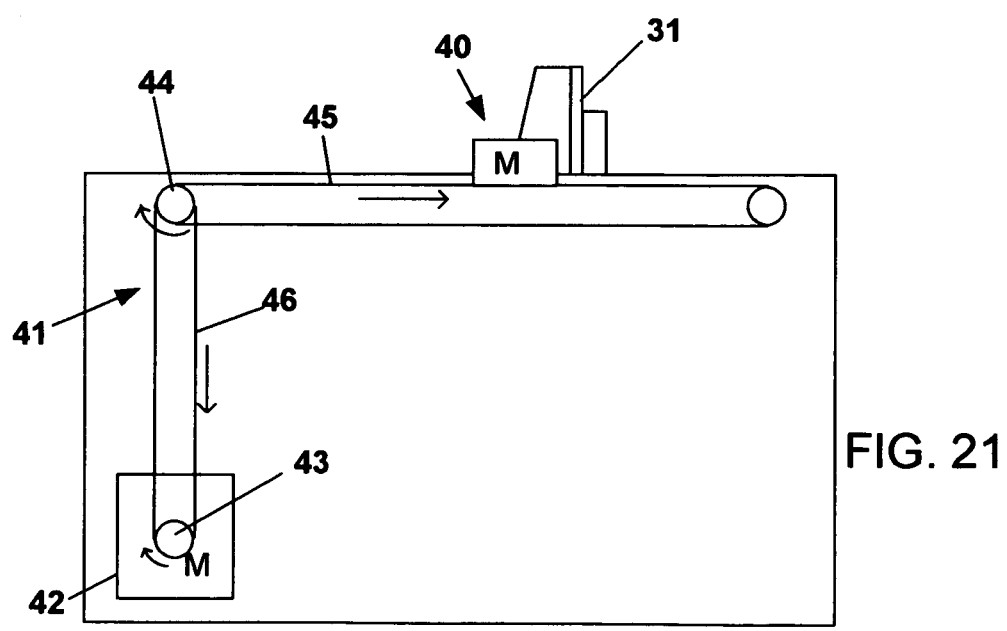

In FIGS. 20 and 21, linear actuators 40 and 41 have been controlled by computer 32 to position robotic syringe grabber 31 over dispenser 3b7. Linear actuators 40 and 41 are preferably belt-driven linear actuators. Motor 42 has turned wheel 43 clockwise. The clockwise motion of wheel 43 has caused belt 46, wheel 44 and belt 45 to also turn clockwise. The clockwise motion of belt 45 has caused linear actuator 40 to move to the right (FIG. 21) so that linear actuator 40 is just above the row of dispensers having dispenser 3b7 (FIG. 20). Concurrently, motor 47 of linear actuator 40 has turned wheel 48 clockwise causing belt 49 to turn clockwise. The clockwise motion of belt 49 has caused robotic syringe grabber 31 to move to the left (FIG. 20) so that it is positioned above dispenser 3b7.

Figure 22:
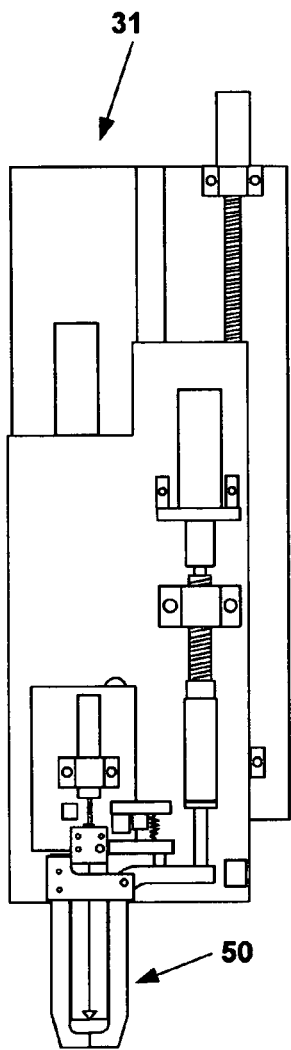

FIG. 22 shows a front view of robotic syringe grabber 31 positioned over dispenser 3b7. Gripper 50 is positioned slightly to the left of the vertical center of dispenser 3b7.

Figure 23:
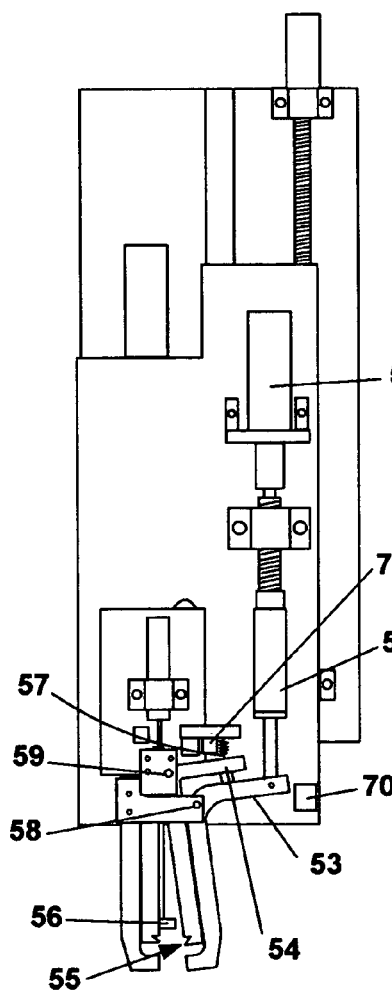

In FIG. 23 motor 51 has controlled linkage 52 so that it has pulled upward on syringe gripper arm 53 of syringe gripper 50 causing syringe gripper arm 53 to turn counter-clockwise about axis 58. The counterclockwise motion of syringe gripper arm 53 has pushed syringe plunger arm 54 counterclockwise about axis 59 compressing linear spring 57. The counterclockwise rotations of syringe gripper 50 and plunger gripper 55 have exposed plunger foot 56. Sensor 70 verifies that syringe gripper 50 is open and sensor 71 verifies that plunger gripper 55 is open.

Figure 24:
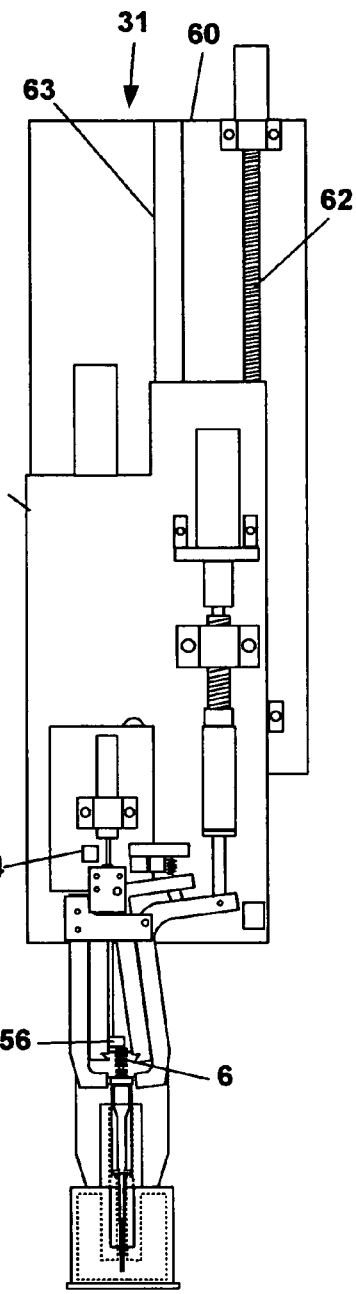

In FIG. 24 a linear actuator motor (not shown) of linear actuator 60 has turned screw 62 of robotic syringe grabber 31 causing platform 61 to move downward on track 63 of linear actuator 60. Platform 61 has moved downward until plunger foot 56 has contacted plunger 6. Plunger present sensor 64 verifies that plunger foot 56 has contacted plunger 6.

Figure 25:
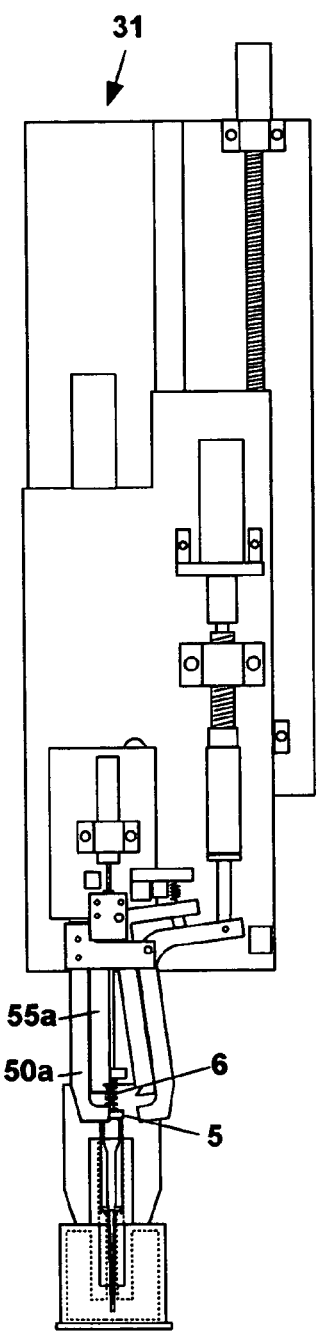

In FIG. 25 computer 32 has moved robotic syringe gripper 31 slightly to the right so that fixed syringe gripper jaw 50a and fixed plunger gripper jaw 55a engage syringe 5 and plunger 6, respectively.

Figure 26:
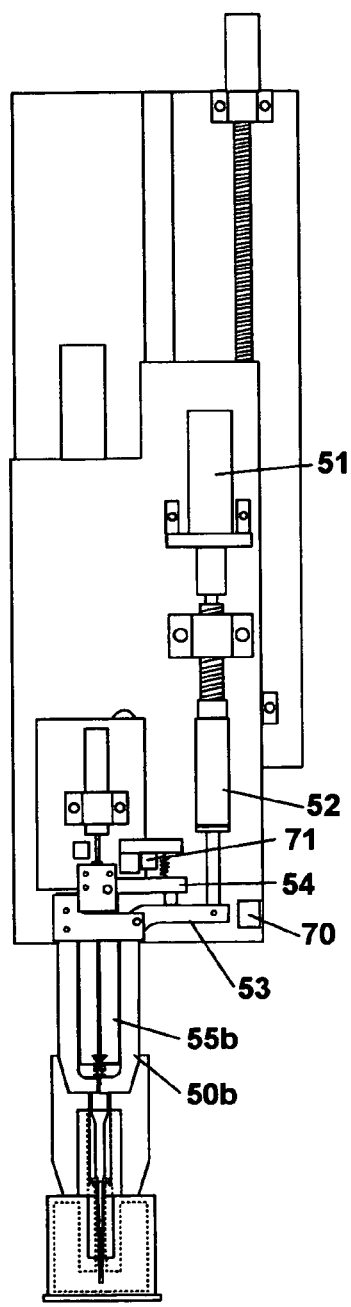

In FIG. 26 motor 51 has controlled linkage 52 so that it has lowered syringe gripper arm 53 of syringe gripper 50 causing syringe gripper arm 53 to turn clockwise. The clockwise motion of syringe gripper arm 53 has allowed linear spring 57 to push syringe plunger arm 54 clockwise. The clockwise rotations of syringe gripper arm 53 and syringe plunger arm 54 have caused syringe gripper jaw 50b and plunger gripper jaw 55b to engage syringe 5 and plunger 6, respectively. Sensor 70 verifies that syringe gripper 50 is closed and not jammed and sensor 71 verifies that plunger gripper 55 is closed and not jammed.

Figure 27:
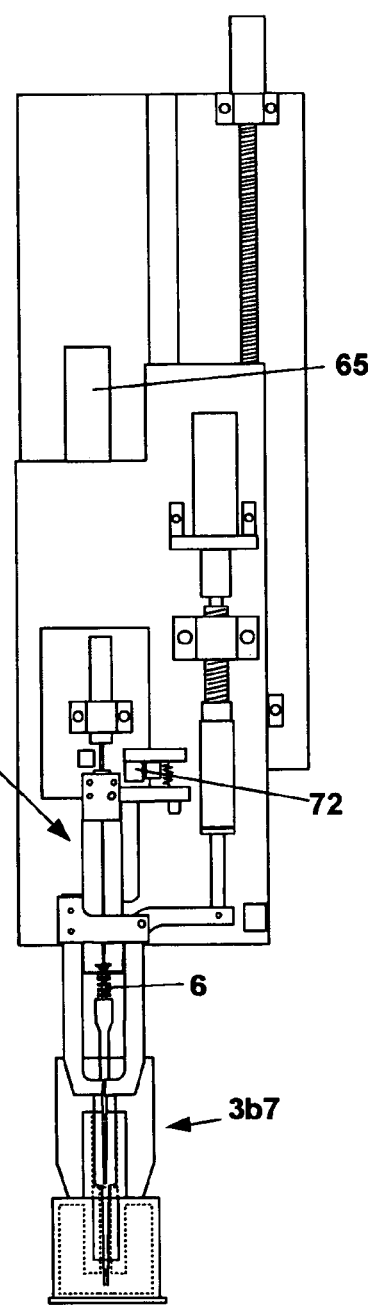
Figure 27B:
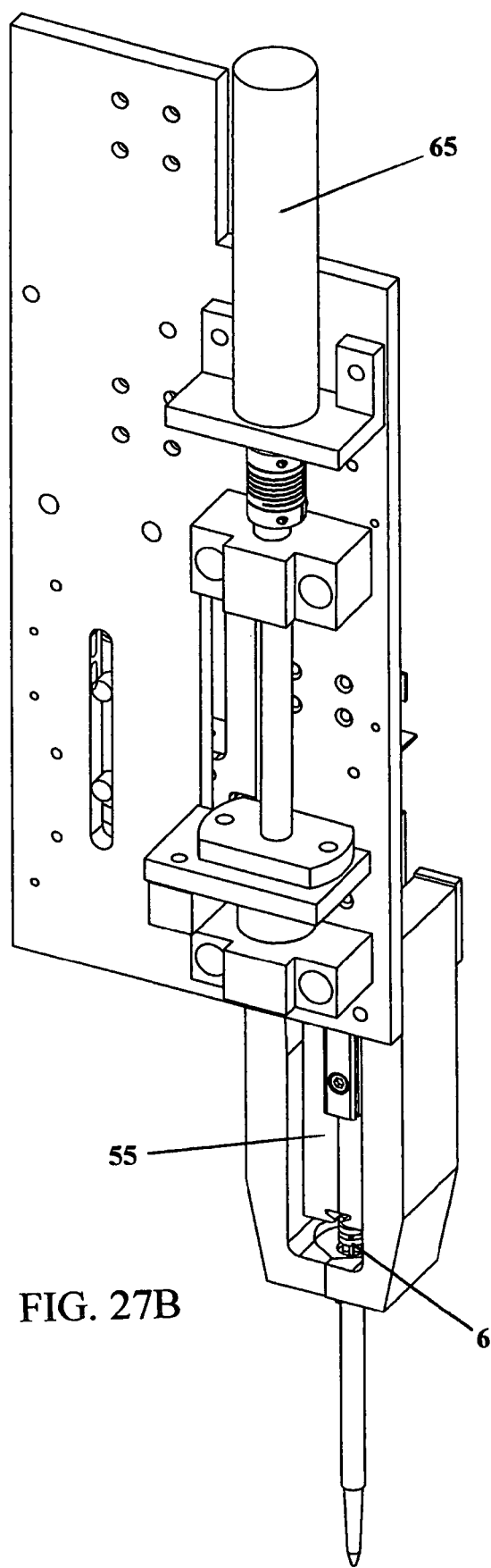

In FIG. 27 plunger motor 65 has raised plunger gripper 55 as shown. A rear perspective view of plunger motor 65 and plunger gripper 55 is shown in FIG. 27B. Plunger gripper 55 is gripping plunger 6. Therefore, plunger 6 has also been raised. The raising of plunger 6 has drawn liquid from dispenser 3b7 (FIG. 27) inside syringe 5 in a fashion similar to that described above in reference to FIG. 9. While liquid is being drawn into syringe 5, the force on plunger 6 is monitored by sensor 72. If the force is outside of acceptable parameters, a warning will be displayed. If the pressure is too low, the plunger may be drawing in air along with the liquid. If the pressure is too high, there may be an obstruction blocking the tip of the plunger.

Figure 28:
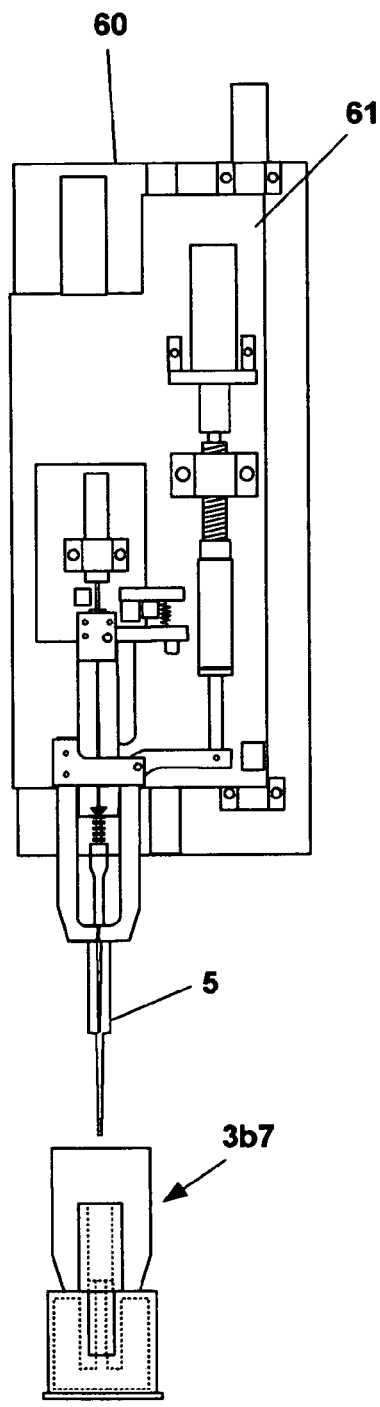

In FIG. 28 linear actuator 60 has raised platform 61 so that syringe 5 is at sufficient height to clear dispenser 3b7.

Figure 29:
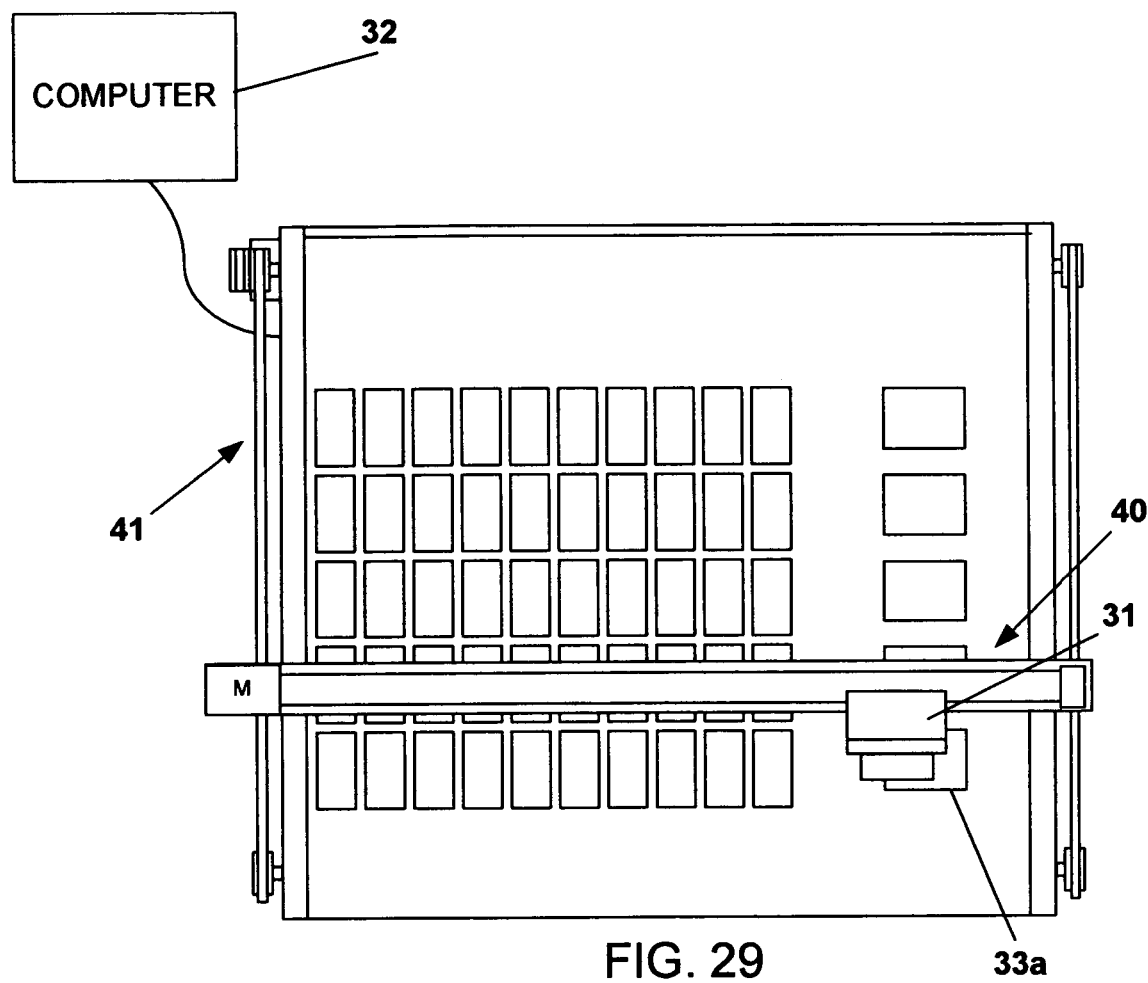
Figure 30:
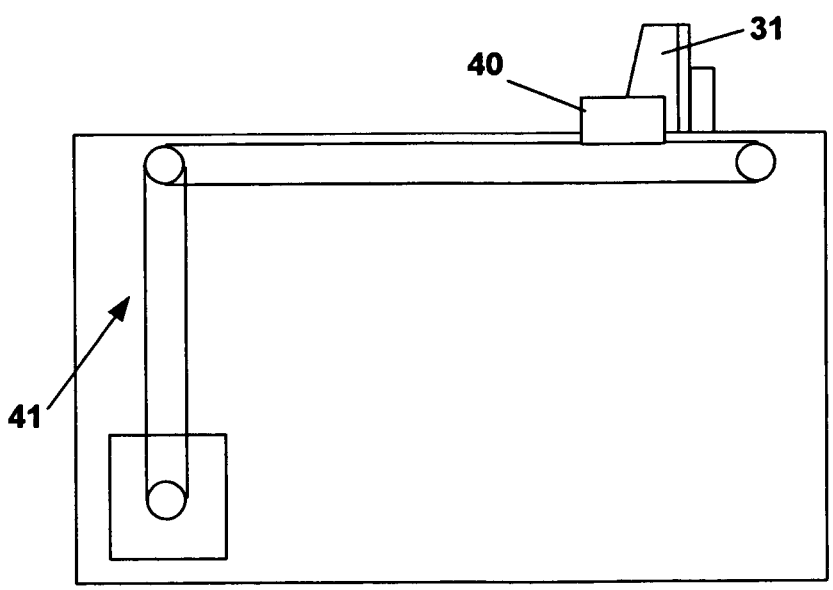

In FIGS. 29 and 30 linear actuators 40 and 41 have been controlled by computer 32 to position robotic syringe grabber 31 over micro-well plate 33a.

Figure 31:
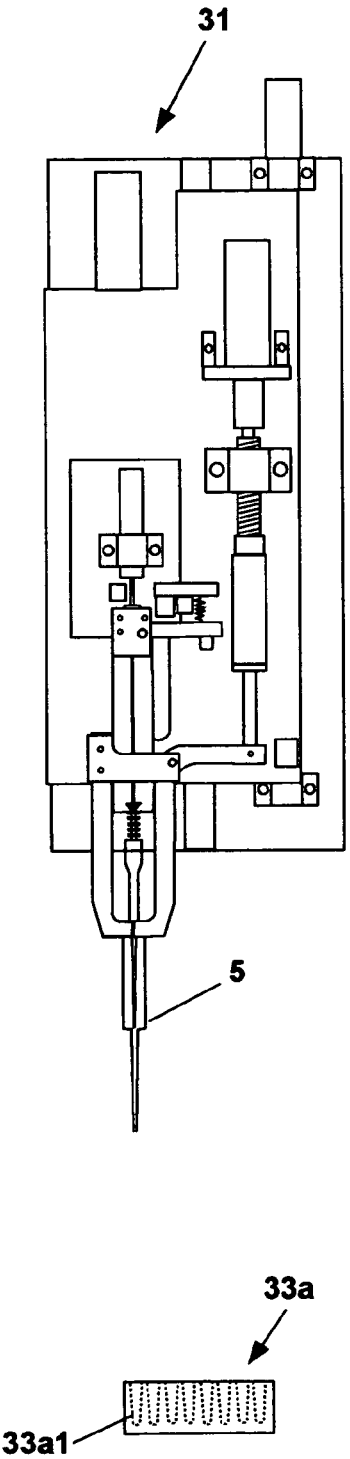

FIG. 31 shows a side view of robotic syringe grabber 31 holding syringe 5 so that it is positioned over well 33a1 of micro-well plate 33a.

Figure 32:
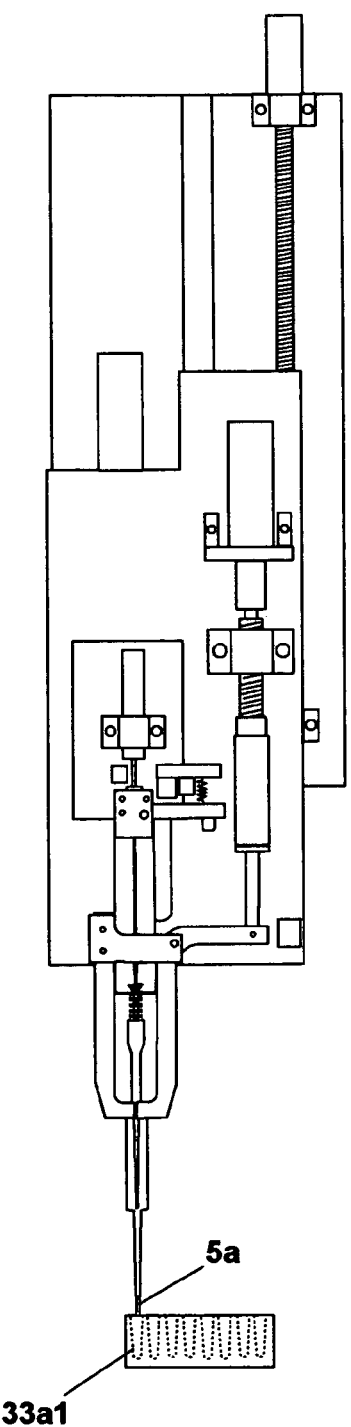

In FIG. 32 linear actuator 60 has lowered platform 61 so that tip 5a of syringe 5 is positioned at a position just above the top of well 33a1.

Figure 33:
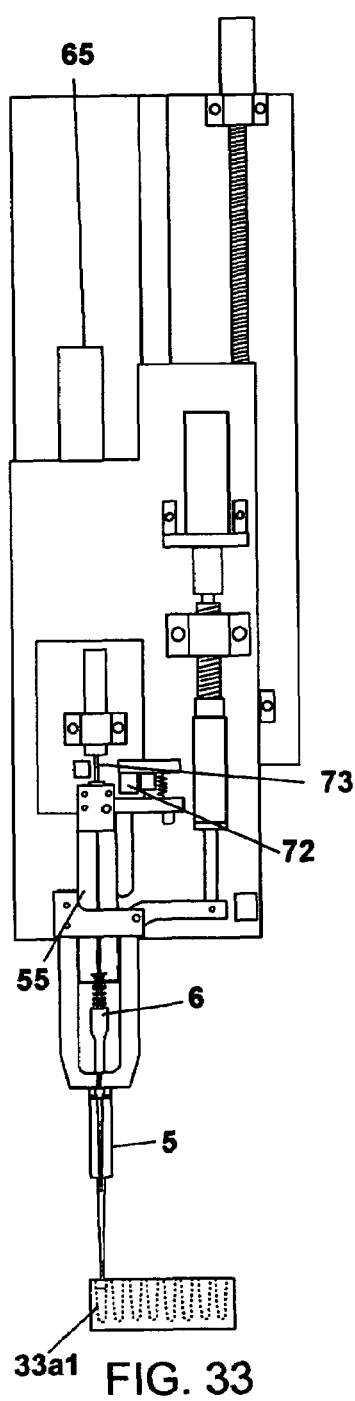

In FIG. 33 plunger motor 65 has lowered plunger gripper 55 causing plunger 6 to be pressed downward. Again, the force on plunger 6 has been monitored by sensor 72. Actuator 73 has been momentarily activated to cause its core rod to bump the top of plunger gripper 55. The repeated bumping has generated shock waves that have been transmitted through plunger gripper 55 to plunger 6 and to syringe 5. The shock waves serve to dislodge any drops that may be adhering to the tip of syringe 5. As shown in FIG. 33, a small amount of liquid has been dispensed into well 33a1.

Figure 34:
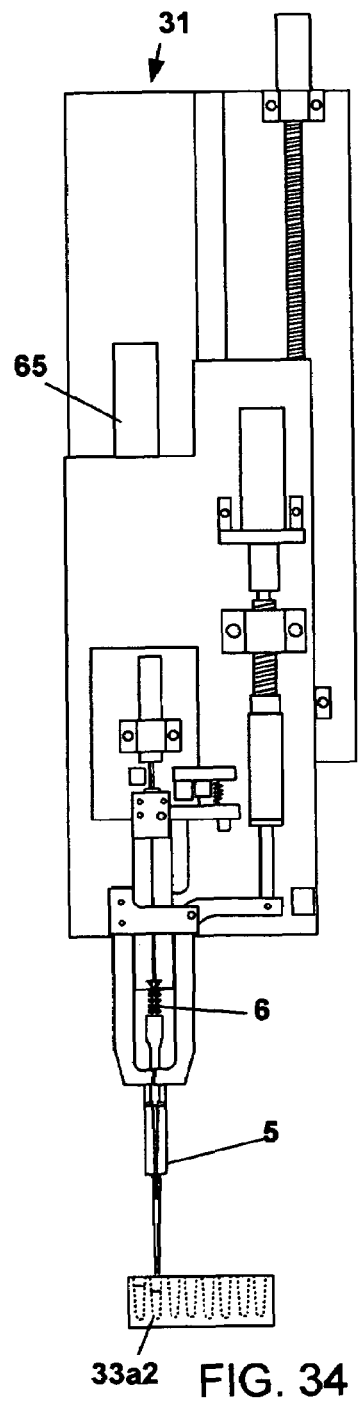

In FIG. 34 linear actuator 40 (FIG. 29) has moved robotic syringe grabber 31 slightly to the right so that syringe 5 is positioned above well 33a2. Plunger motor 65 has further lowered plunger gripper 55 causing plunger 6 to be pressed downward. Actuator 73 has been activated. A small amount of liquid has been dispensed into well 33a2.

Figure 35:
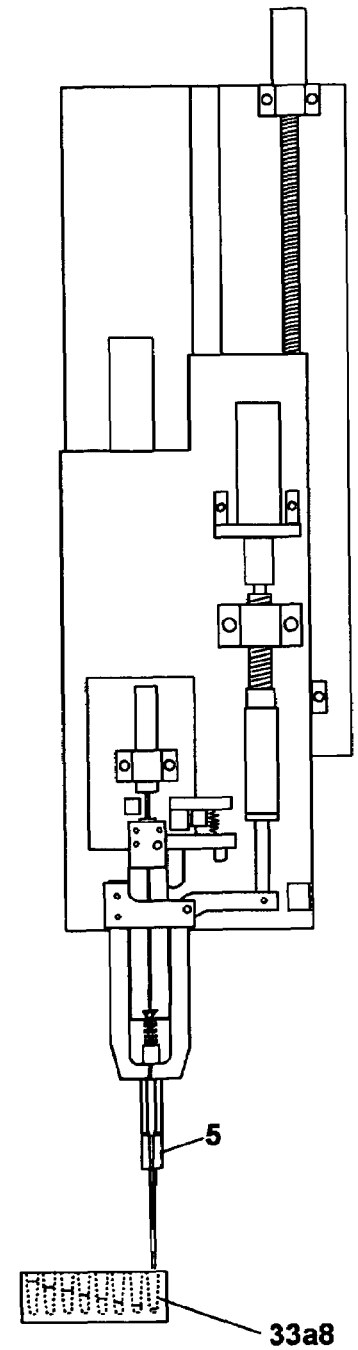

FIG. 35 shows syringe 5 positioned above well 33a8. In a fashion similar to that described in reference to FIGS. 33 and 34, small amounts of liquid have been dispensed in wells 33a3-33a8.

Figures 36, 37, 38:
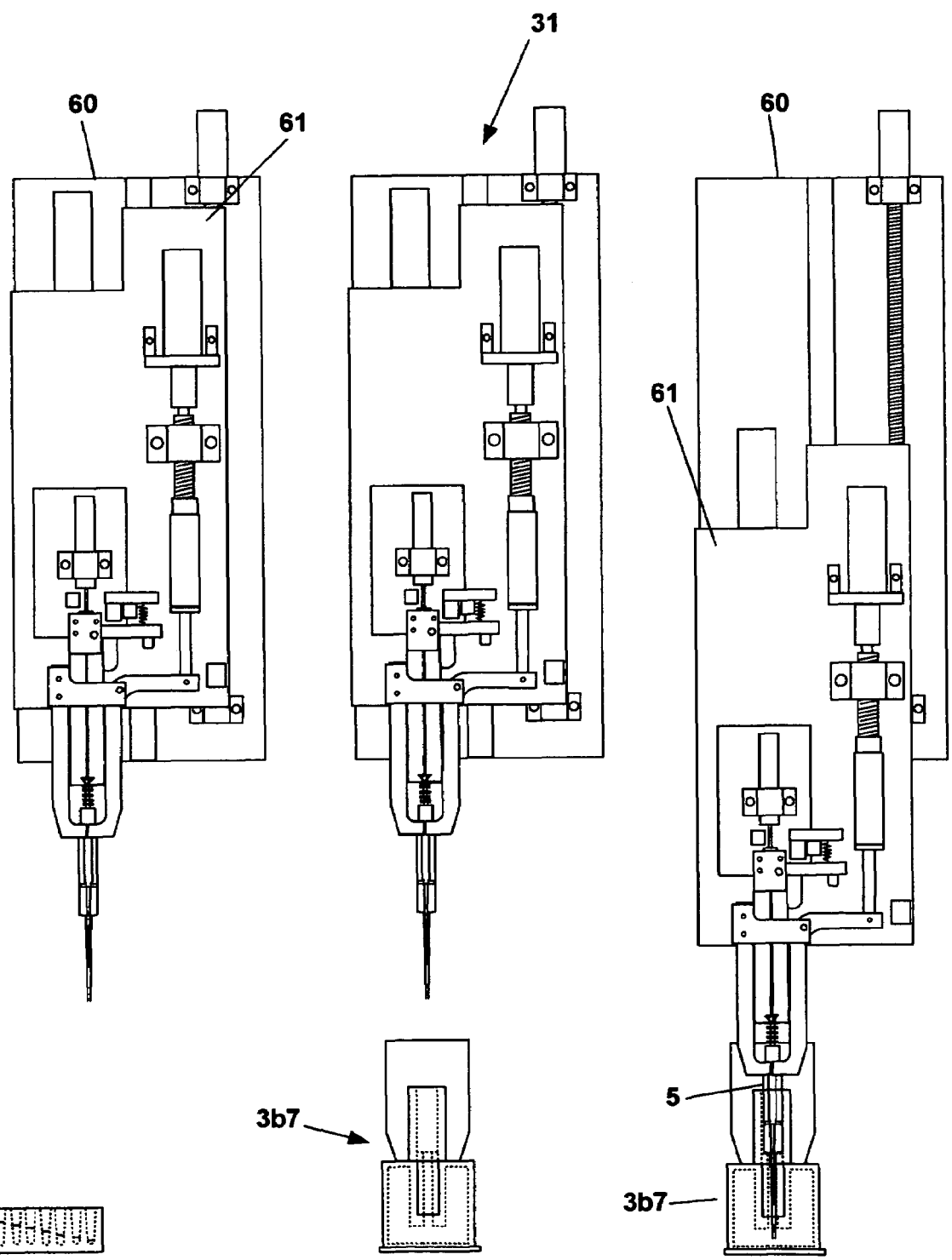

In FIG. 36 linear actuator 60 has raised platform 61.

In FIG. 37, linear actuators 40 and 41 have positioned robotic syringe grabber 31 over dispenser 3b7 (see also FIGS. 20 and 21).

In FIG. 38 linear actuator 60 has lowered platform 61 so that syringe 5 is inside dispenser 3b7.

Figure 39:
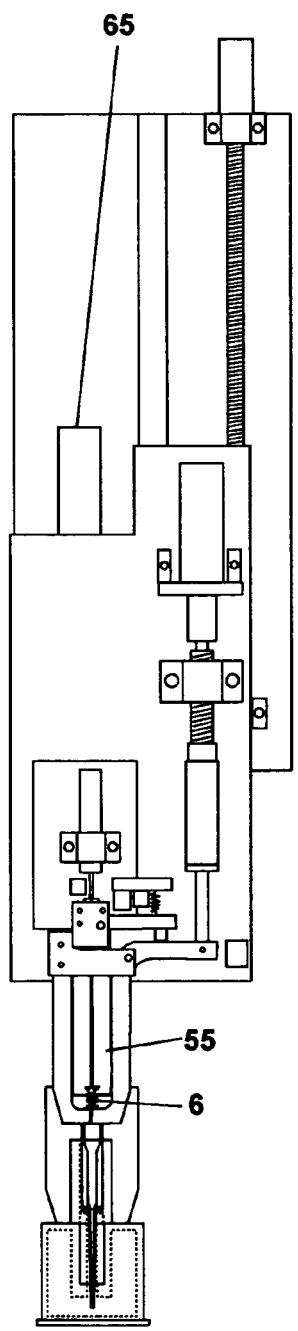

In FIG. 39 plunger motor 65 has lowered plunger gripper 55 causing plunger 6 to be pressed downward. The remaining amount of liquid inside syringe 5 has been returned to dispenser 3b7.

Figure 40:
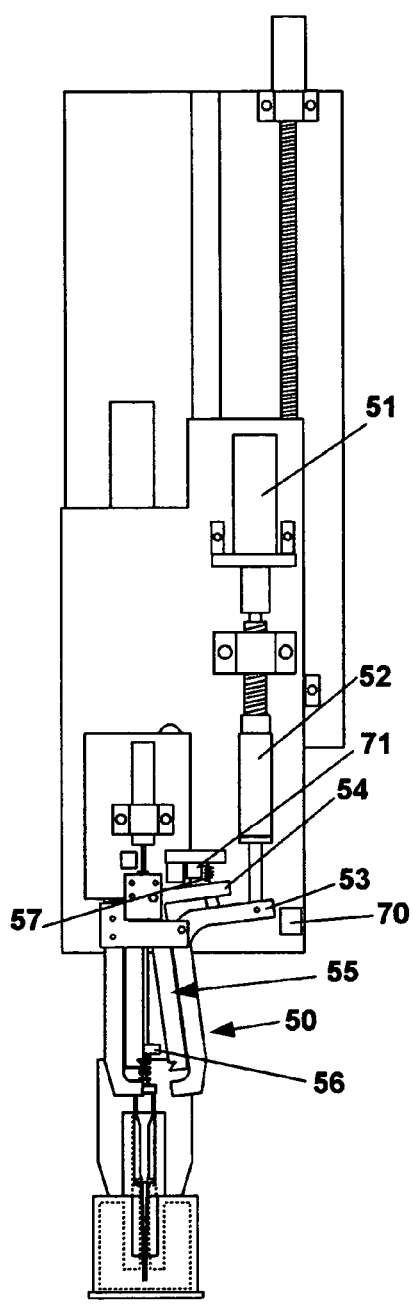

In FIG. 40 motor 51 has controlled linkage 52 so that it has pulled upward on syringe gripper arm 53 of syringe gripper 50 causing syringe gripper arm 53 to turn counter-clockwise about axis 58. The counterclockwise motion of syringe gripper arm 53 has pushed syringe plunger arm 54 counterclockwise about axis 59 compressing linear spring 57. The counterclockwise rotations of syringe gripper 50 and plunger gripper 55 have exposed plunger foot 56. Sensor 70 verifies that syringe gripper 50 is open and sensor 71 verifies that plunger gripper 55 is open.

Figure 41:
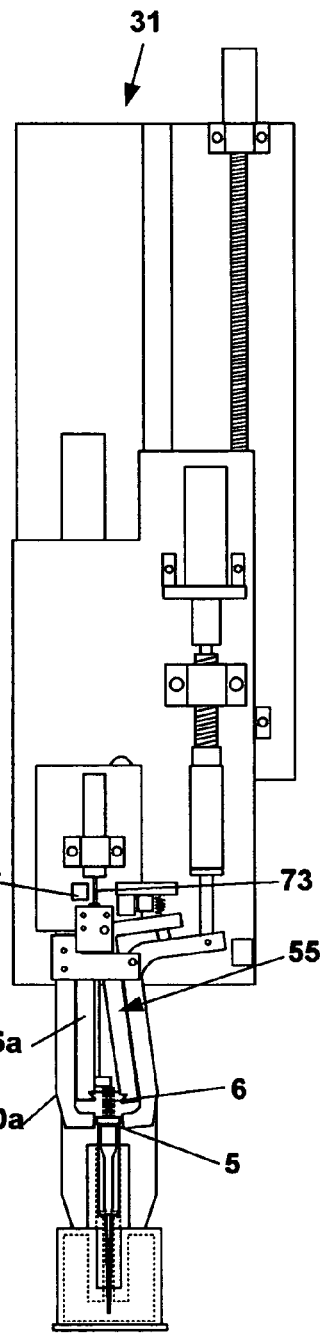

In FIG. 41 linear actuator 40 (FIG. 20) has moved robotic syringe gripper 31 slightly to the left to disengage fixed syringe gripper jaw 50a and fixed plunger gripper jaw 55a from syringe 5 and plunger 6, respectively. Actuator 73 has been activated to bump on the top of plunger gripper 55. The bumping creates shock waves that travel through plunger gripper 55 and syringe gripper 50. The shock waves help ensure that syringe 5 and plunger 6 are totally released from plunger gripper 55 and syringe gripper 50. Plunger present sensor 64 verifies that syringe and plunger have been totally released.

Figure 42:
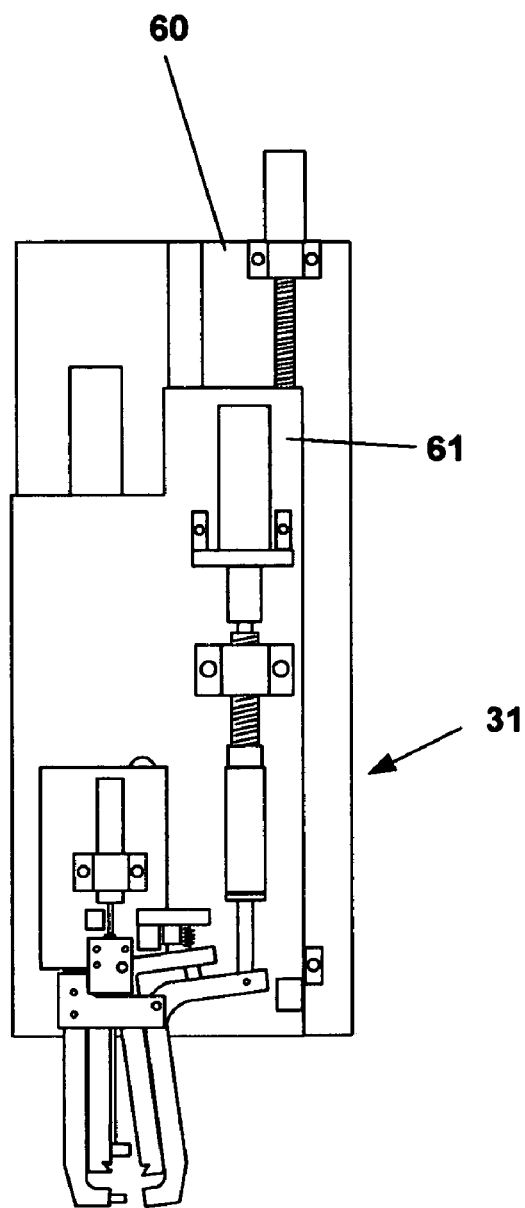
Figure 42:
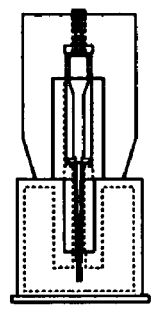

In FIG. 42 linear actuator 60 has raised platform 61. Robotic syringe gripper 31 can now be positioned above another dispenser to remove liquid in a fashion similar to that described above.

For example, in one preferred embodiment robotic syringe gripper 31 is positioned over dispenser 3a1 to remove liquid contained in dispenser 3a1. The solution in dispenser 3a1 is different than the solution in dispenser 3b7. After removing the solution from dispenser 3a1, robotic syringe gripper 31 deposits the solution into wells 33a1-33a8 (FIGS. 33-35) in a fashion similar to that described above. The solutions from dispensers 3a1 and 3b7 are consequently mixed inside the wells of micro-well plate 33a to form a chemical solution suitable for use in proteomic crystal trials in protein crystallography.

Locating Indentations

Figure 43:
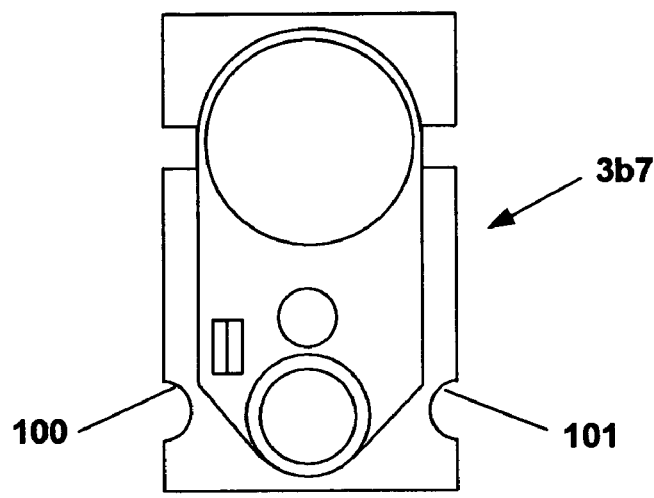
FIGS. 43-44 show the utilization of locating indentations.
Figure 44:
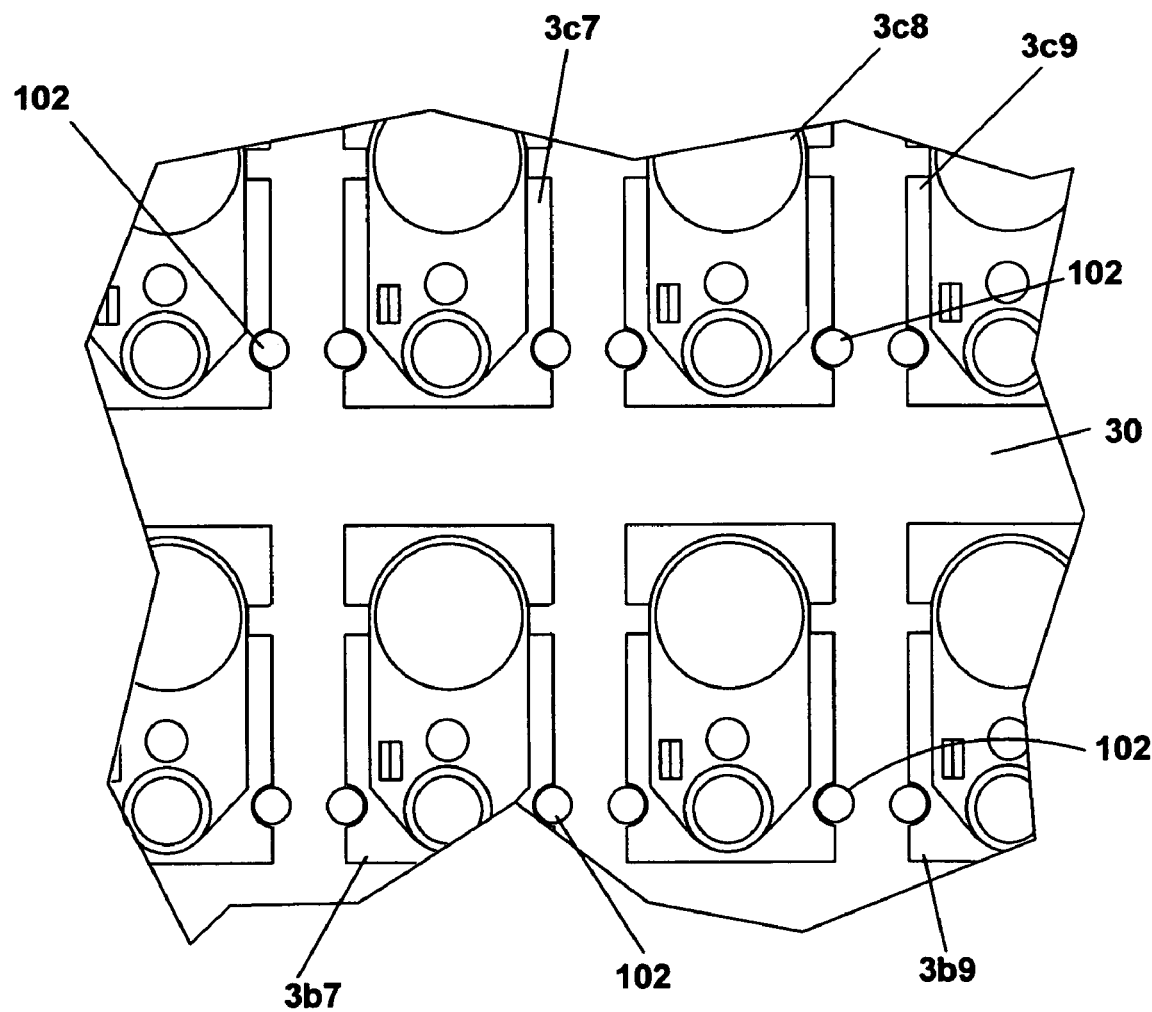

In the third preferred embodiment, dispensers 3a1-3e10 include locating indentations 100 and 101 (FIG. 43). FIG. 43 shows a top view of dispenser 3b7 with locating indentations 101 and 100. FIG. 2A also shows a perspective view of locating indentations 100 and 101. Platform 30 includes locating pins 102 arranged as shown in FIG. 44. Dispensers 3a1-3e10 are arranged on platform 30 so that locating indentations 100 and 101 are aligned with locating pins 102. By utilization of locating pins 102 and locating indentations 100 and 101, dispensers 3a1-3e10 can be precisely positioned on platform 30 and undesirable movement of the dispensers can be virtually eliminated.

Although the above-preferred embodiments have been described with specificity, persons skilled in this art will recognize that many changes to the specific embodiments disclosed above could be made without departing from the spirit of the invention. For example, bottle 1 (FIG. 2B) can be made out of other materials besides plastic. In one preferred embodiment, for example, bottle 1 is glass. Also, retaining clip 4 can be made out of variety of materials such as plastic or metal. Also, tilted bottom component 9 can be molded such that its vertical sides extend up inside dispenser 3 to a height that is higher than the dispensing level. This would help minimize that possibility of liquid leaking through the connection of bottom component 9. Also, although it was described in detail how robotic syringe grabber 31 (FIG. 17) is utilized to remove syringes from dispensers 3a1-3e10, it should be recognized that robotic syringe grabber 31 can also be utilized to similarly remove syringes from a variety of dispenser types for the purpose of dispensing liquid. For example, robotic syringe grabber 31 can be used to remove a syringe from a simple bottle having a syringe positioned at its opening. Therefore, the attached claims and their legal equivalents should determine the scope of the invention.

What is claimed is:

1. A liquid dispensing device, comprising:
  A. a tray for holding a liquid at a relatively constant level defining an approximately constant tray liquid level,
  B. a liquid container containing a liquid having an opening and positioned upside-down in said tray with the opening defining a vertical position approximately equal to or below the relatively constant tray liquid level such that atmospheric pressure on the liquid in said tray and vacuum inside said container prevents liquid from draining from said container except when the liquid level is said tray drops to a level approximately equal to or below to the vertical position of said opening, and
  C. a syringe for drawing liquid from said tray,
    wherein positioning of said syringe for drawing fluid is simplified by reason of the fact that the level of fluid in said tray is maintained at an approximately constant level despite withdrawal of quantities of fluid from said tray.

2. The liquid dispensing device as in claim 1, further comprising a retaining clip for attaching said upside-down container to said liquid dispensing device.

3. The liquid dispensing device as in claim 1, further comprising an air filter for filtering air entering said liquid dispensing device.

4. The liquid dispensing device as in claim 1, further comprising a tilted bottom component for puddling liquid below said syringe.

5. The liquid dispensing device as in claim 1, further comprising a liquid level indicator.

6. The liquid dispensing device as in claim 1, wherein said syringe is manually removably inserted into said liquid dispensing device by the hand of an operator.

7. The liquid dispensing device as in claim 1, wherein said syringe is automatically removably inserted into said liquid dispensing device by the utilization of an automated liquid mixing device, and wherein liquid is automatically transferred to a liquid receiving device.

8. The liquid dispensing device as in claim 7, wherein said liquid receiving device is a micro-well plate.

9. The liquid dispensing device as in claim 7, wherein said liquid dispensing device is at least one liquid dispensing device, wherein said automated liquid handling device comprises:
  A. a robotic syringe grabber positionable above said at least one liquid dispensing device,
  B. at least one horizontal positioning linear actuator for horizontally positioning said robotic syringe grabber above said at least one liquid dispensing device, and
  C. a computer programmed to control said at least one horizontal positioning linear actuator and said robotic syringe grabber.

10. The liquid dispensing device as in claim 9, wherein said syringe comprises a plunger, wherein said robotic syringe grabber comprises:
  A. a linear actuator for vertically positioning said robotic syringe grabber at the height of said syringe and for lifting said syringe clear of said at least one dispensing device, and for positioning said robotic syringe grabber at the height of said liquid receiving device
  B. a syringe gripper for gripping said syringe,
  C. a plunger gripper for gripping said plunger, and
  D. a second linear actuator for raising said plunger to draw liquid into said syringe and for lowering said plunger to dispense liquid into said liquid receiving device.

11. The liquid dispensing device as in claim 10, wherein said robotic syringe grabber further comprises an actuator for transmitting shock waves to said syringe, wherein said shock waves are utilized to dislodge drops of liquid adhering to said syringe.

12. The liquid dispensing device as in claim 7, wherein said liquid dispensing device is a plurality of liquid dispensing devices arranged on a platform, wherein each of said plurality of liquid dispensing devices comprises at least one locating indentation, wherein said platform comprises at least one locating pin, wherein said at least one indentation is aligned with said at least one locating pin.

13. A liquid dispensing device, comprising:
  A. a tray means for holding a liquid at a relatively constant level defining an approximately constant tray liquid level,
  B. a liquid container means containing a liquid having an opening and positioned upside-down in said tray with the opening defining a vertical position approximately equal to or below the relatively constant tray fluid level such that atmospheric pressure on the liquid in said tray means and vacuum inside said container means prevents liquid from draining from said container means except when the fluid level in said tray means drops to a level approximately equal to or below the vertical position of said opening, and
  C. a syringe means for drawing fluid from said tray means,
    wherein positioning of said syringe means for drawing fluid is simplified by reason of the fact that the level of fluid in said tray means is maintained at an approximately constant level despite withdrawal of quantities of fluid from said tray means.

14. The liquid dispensing device as in claim 13, further comprising a retaining clip means for attaching said container means to said liquid dispensing device.

15. The liquid dispensing device as in claim 13, further comprising an air filter means for filtering air entering said liquid dispensing device.

16. The liquid dispensing device as in claim 13, further comprising a tilted bottom means for puddling liquid below said syringe means.

17. The liquid dispensing device as in claim 13, further comprising a liquid level indicator means.

18. The liquid dispensing device as in claim 13, wherein said syringe means is manually removably inserted into said liquid dispensing device by the hand of an operator.

19. The liquid dispensing device as in claim 13, wherein said syringe means is automatically removably inserted into said liquid dispensing device by the utilization of an automated liquid mixing means, and wherein liquid is automatically transferred to a liquid receiving means.

20. The liquid dispensing device as in claim 19, wherein said liquid receiving means is a micro-well plate.

21. The liquid dispensing device as in claim 19, wherein said liquid dispensing device is at least one liquid dispensing device, wherein said automated liquid handling means comprises:
  A. a robotic syringe grabber means positionable above said at least one liquid dispensing device,
  B. at least one horizontal positioning linear actuator means for horizontally positioning said robotic syringe grabber means above said at least one liquid dispensing device, and
  C. a computer means programmed to control said at least one horizontal positioning linear actuator means and said robotic syringe grabber means.

22. The liquid dispensing device as in claim 21, wherein said syringe comprises a plunger means, wherein said robotic syringe grabber means comprises:
  A. a linear actuator means for vertically positioning said robotic syringe grabber means at the height of said syringe means and for lifting said syringe means clear of said at least one liquid dispensing device, and for positioning said robotic syringe grabber means at the height of said liquid receiving means,
  B. a syringe gripper means for gripping said syringe means,
  C. a plunger gripper means for gripping said plunger means, and
  D. a second linear actuator means for raising said plunger means to draw liquid into said syringe means and for lowering said plunger means to dispense liquid into said liquid receiving means.

23. The liquid dispensing device as in claim 22, wherein said robotic syringe grabber means further comprises an actuator means for transmitting shock waves to said syringe means, wherein said shock waves are utilized to dislodge drops of liquid adhering to said syringe means.

24. The liquid dispensing device as in claim 19, wherein said liquid dispensing device is a plurality of liquid dispensing devices arranged on a platform means, wherein each of said plurality of liquid dispensing devices comprises at least one locating indentation means, wherein said platform means comprises at least one locating pin means, wherein said at least one indentation means is aligned with said at least one locating pin means.

25. A method for dispensing liquid, comprising the steps of:
  A. inserting a syringe into a liquid dispensing device, wherein said liquid dispensing device comprises:
    1. a tray for holding a liquid at a relatively constant level defining an approximately constant tray liquid level, and
    2. a liquid container containing a liquid having an opening and positioned upside-down in said tray with the opening defining a vertical position approximately equal to or below the relatively constant tray liquid level such that atmospheric pressure on the liquid in said tray and vacuum inside said container prevents liquid from draining from said container except when the liquid level is said tray drops to a level approximately equal to or below to the vertical position of said opening, wherein positioning of said syringe for drawing fluid is simplified by reason of the fact that the level of fluid in said tray is maintained at an approximately constant level despite withdrawal of quantities of fluid from said tray,
  B. drawing liquid into said syringe,
  C. removing said syringe from said liquid dispensing device, and
  D. dispensing liquid from said syringe into a liquid receiving device.

26. The method as in claim 25, wherein said liquid dispensing device further comprises a retaining clip for attaching said liquid container to said liquid dispensing device.

27. The method as in claim 25, wherein said liquid dispensing device further comprises an air filter for filtering air entering said liquid dispensing device.

28. The method as in claim 25, wherein said liquid dispensing device further comprises a tilted bottom component for puddling liquid below said syringe tip.

29. The method as in claim 25, wherein said liquid dispensing device further comprises a liquid level indicator.

30. The method as in claim 25, wherein said syringe is manually removably inserted into said liquid dispensing device by the hand of an operator.

31. The method as in claim 25, wherein said syringe is automatically removably inserted into said liquid dispensing device by the utilization of an automated liquid mixing device, and wherein liquid is automatically transferred to said liquid receiving device.

32. The method as in claim 31, wherein said liquid receiving device is a micro-well plate.

33. The method as in claim 31, wherein said liquid dispensing device is at least one liquid dispensing device, wherein said automated liquid handling device comprises:
   A. a robotic syringe grabber positionable above said at least one liquid dispensing device,
   B. at least one horizontal positioning linear actuator for horizontally positioning said robotic syringe grabber above said at least one liquid dispensing device, and
   C. a computer programmed to control said at least one horizontal positioning linear actuator and said robotic syringe grabber.

34. The method as in claim 33, wherein said syringe comprises a plunger, wherein said robotic syringe grabber comprises:
   A. a linear actuator for vertically positioning said robotic syringe grabber at the height of said syringe and for lifting said syringe clear of said at least one dispensing device, and for positioning said robotic syringe grabber at the height of said liquid receiving device
   B. a syringe gripper for gripping said syringe,
   C. a plunger gripper for gripping said plunger, and
   D. a second linear actuator for raising said plunger to draw liquid into said syringe and for lowering said plunger to dispense liquid into said liquid receiving device.

35. The method as in claim 34, wherein said robotic syringe grabber further comprises an actuator for transmitting shock waves to said syringe, wherein said shock waves are utilized to dislodge drops of liquid adhering to said syringe.

36. The method as in claim 31, wherein said liquid dispensing device is a plurality of liquid dispensing devices arranged on a platform, wherein each of said plurality of liquid dispensing devices comprises at least one locating indentation, wherein said platform comprises at least one locating pin, wherein said at least one indentation is aligned with said at least one locating pin.

37. A liquid dispensing device, comprising:
   A. a tray for holding a liquid,
   B. a liquid container containing a liquid having an opening and positioned upside-down in said tray with the opening defining a vertical position such that liquid from said container maintains a liquid level in said tray at an approximately constant liquid level that is sufficient to maintain a vacuum in said container such that atmospheric pressure on the liquid in said tray and the vacuum inside said container prevents liquid from draining from said container except when the liquid level in said tray drops to a level in relation to the vertical position of said opening sufficient to permit a small quantity of liquid to drain from said container and to permit a small quantity of air to enter said container slightly reducing said vacuum, and
   C. a syringe for drawing fluid from said tray, wherein positioning of said syringe for drawing fluid is simplified by reason of the fact that the level of liquid in said tray is maintained at an approximately constant level despite withdrawal of quantities of liquid from said tray.

38. The liquid dispensing device as in claim 37, further comprising a retaining clip for attaching said upside-down container to said liquid dispensing device.

39. The liquid dispensing device as in claim 37, further comprising an air filter for filtering air entering said liquid dispensing device.

40. The liquid dispensing device as in claim 37, further comprising a tilted bottom component for puddling liquid below said syringe.

41. The liquid dispensing device as in claim 37, further comprising a liquid level indicator.

42. The liquid dispensing device as in claim 37, wherein said syringe is manually removably inserted into said liquid dispensing device by the hand of an operator.

43. The liquid dispensing device as in claim 37, wherein said syringe is automatically removably inserted into said liquid dispensing device by the utilization of an automated liquid mixing device, and wherein liquid is automatically transferred to a liquid receiving device.

44. The liquid dispensing device as in claim 43, wherein said liquid receiving device is a micro-well plate.

45. The liquid dispensing device as in claim 43, wherein said liquid dispensing device is at least one liquid dispensing device, wherein said automated liquid handling device comprises:
   A. a robotic syringe grabber positionable above said at least one liquid dispensing device,
   B. at least one horizontal positioning linear actuator for horizontally positioning said robotic syringe grabber above said at least one liquid dispensing device, and
   C. a computer programmed to control said at least one horizontal positioning linear actuator and said robotic syringe grabber.

46. The liquid dispensing device as in claim 45, wherein said syringe comprises a plunger, wherein said robotic syringe grabber comprises:
   A. a linear actuator for vertically positioning said robotic syringe grabber at the height of said syringe and for lifting said syringe clear of said at least one dispensing device, and for positioning said robotic syringe grabber at the height of said liquid receiving device
   B. a syringe gripper for gripping said syringe,
   C. a plunger gripper for gripping said plunger, and
   D. a second linear actuator for raising said plunger to draw liquid into said syringe and for lowering said plunger to dispense liquid into said liquid receiving device.

47. The liquid dispensing device as in claim 46, wherein said robotic syringe grabber further comprises an actuator for transmitting shock waves to said syringe, wherein said shock waves are utilized to dislodge drops of liquid adhering to said syringe.

48. The liquid dispensing device as in claim 43, wherein said liquid dispensing device is a plurality of liquid dispensing devices arranged on a platform, wherein each of said plurality of liquid dispensing devices comprises at least one locating indentation, wherein said platform comprises at least one locating pin, wherein said at least one indentation is aligned with said at least one locating pin.

* * * * *